United States Patent
Tsunoda et al.

(10) Patent No.: US 6,307,117 B1
(45) Date of Patent: Oct. 23, 2001

(54) METHOD FOR PRODUCING ETHYLENE AND PROPYLENE

(75) Inventors: Takashi Tsunoda; Mitsuhiro Sekiguchi, both of Kurashiki (JP)

(73) Assignee: Asahi Kasei Kogyo Kabushiki Kaisha, Osaka (JP)

( * ) Notice: Subject to any disclaimer, the term of this patent is extended or adjusted under 35 U.S.C. 154(b) by 0 days.

(21) Appl. No.: 09/508,043

(22) PCT Filed: Aug. 25, 1999

(86) PCT No.: PCT/JP99/04592

§ 371 Date: Mar. 3, 2000

§ 102(e) Date: Mar. 3, 2000

(87) PCT Pub. No.: WO00/10948

PCT Pub. Date: Mar. 2, 2000

(30) Foreign Application Priority Data

Aug. 25, 1998 (JP) .................................................. 10-238777

(51) Int. Cl.$^7$ ...................................................... C07C 4/06
(52) U.S. Cl. ........................... 585/651; 585/653; 585/324; 585/330; 208/73; 208/76
(58) Field of Search ..................... 585/651, 653, 585/324, 330; 208/73, 76

(56) References Cited

U.S. PATENT DOCUMENTS

| | | |
|---|---|---|
| 4,324,940 | 4/1982 | Dessau . |
| 4,527,001 | 7/1985 | Kaiser . |
| 4,613,721 | 9/1986 | Kaiser . |
| 5,043,522 | 8/1991 | Leyshon et al. . |
| 5,171,921 | 12/1992 | Gaffney et al. . |
| 5,523,502 | * 6/1996 | Rubin ................................. 585/324 |
| 5,968,342 | 10/1999 | Tsunoda et al. . |
| 6,033,555 | * 3/2000 | Chen et al. ........................ 208/52 R |

FOREIGN PATENT DOCUMENTS

| | | |
|---|---|---|
| 0788838 A1 | 8/1997 | (EP) . |
| 1381427 | 1/1975 | (GB) . |
| 1394979 | 5/1975 | (GB) . |
| 63-10693 | * 1/1988 | (JP) . |
| 8126844 A | 5/1996 | (JP) . |

* cited by examiner

*Primary Examiner*—Walter D. Griffin
(74) *Attorney, Agent, or Firm*—Birch, Stewart, Kolasch & Birch, LLP

(57) ABSTRACT

Disclosed is a method for producing ethylene and propylene from a hydrocarbon feedstock by catalytic conversion, which comprises contacting, in a reactor, a hydrocarbon feedstock comprising 20% by weight or more, based on the weight of the hydrocarbon feedstock, of at least one $C_4$–$C_{12}$ olefin with a zeolite-containing catalyst, wherein the zeolite in the zeolite-containing catalyst satisfies the following requirements: (1) the zeolite is an intermediate pore size zeolite having a pore size of from 5 to 6.5 Å, (2) the zeolite contains substantially no proton, (3) the zeolite contains at least one metal selected from the group consisting of metals belonging to Group IB of the Periodic Table, and (4) the zeolite has an $SiO_2/Al_2O_3$ molar ratio of from 200 to 5,000, to effect a catalytic conversion reaction of the hydrocarbon feedstock, thereby obtaining a reaction mixture containing ethylene and propylene; and separating the ethylene and propylene from the reaction mixture. In the method of the present invention, the zeolite-containing catalyst has high resistance to deactivation and, thus, ethylene and propylene can be stably produced in high yield for a prolonged period of time.

11 Claims, 1 Drawing Sheet

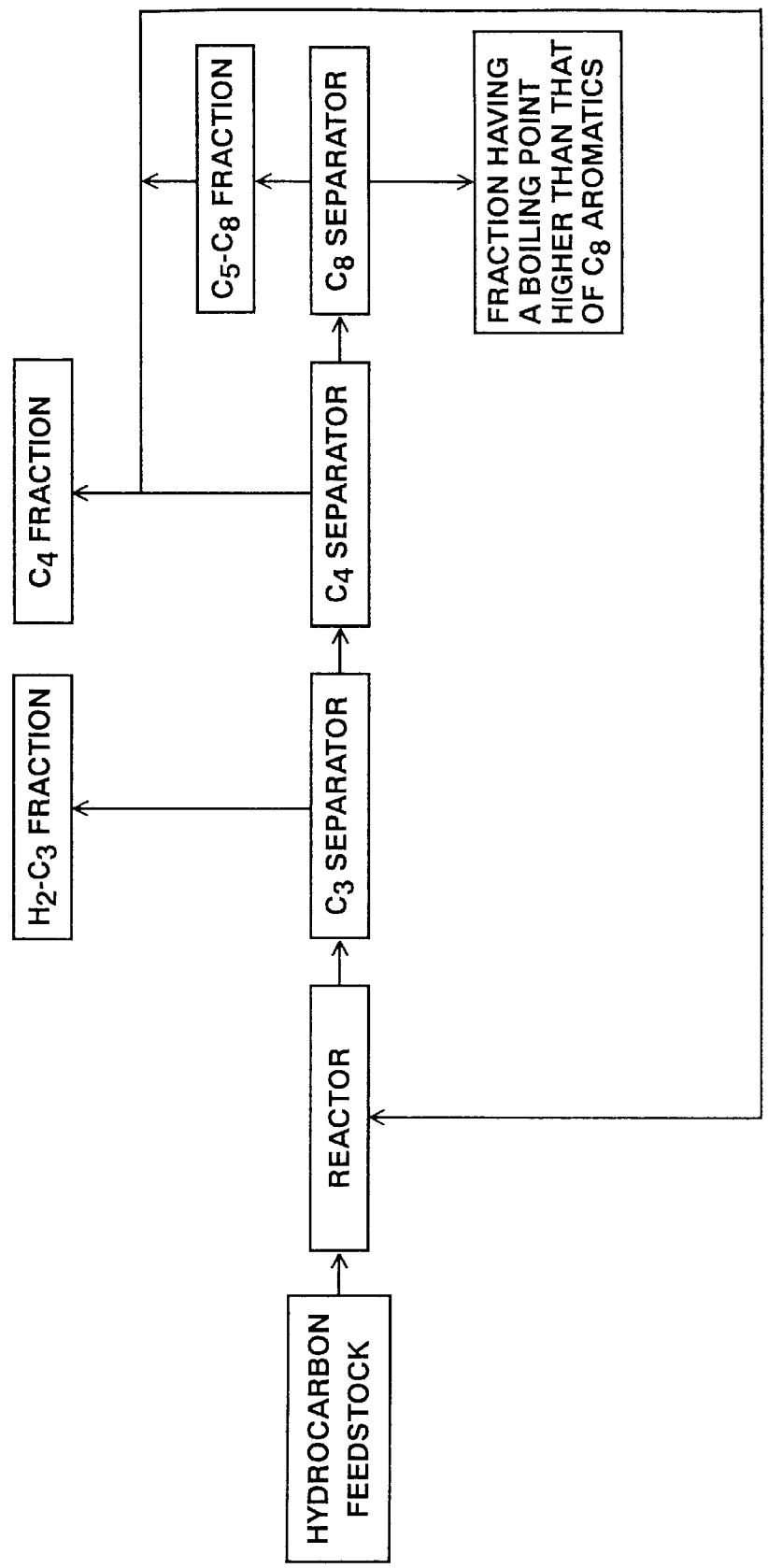

METHOD FOR PRODUCING ETHYLENE AND PROPYLENE

This application is the national phase under 35 U.S.C. § 371 of PCT International Application No. PCT/JP99/04592 which has an International filing date of Aug. 25, 1999, which designated the United States of America.

BACKGROUND OF THE INVENTION

1. Field of the Invention

The present invention relates to a method for producing ethylene and propylene from a hydrocarbon feedstock by catalytic conversion. More particularly, the present invention is concerned with a method for producing ethylene and propylene from a hydrocarbon feedstock by catalytic conversion, which comprises contacting, in a reactor, a hydrocarbon feedstock comprising 20% by weight or more, based on the weight of the hydrocarbon feedstock, of at least one $C_4$–$C_{12}$ olefin with a zeolite-containing catalyst to thereby effect a catalytic conversion reaction of the at least one $C_4$–$C_{12}$ olefin, thereby obtaining a reaction mixture containing ethylene and propylene. In the method of the present invention, not only can ethylene and propylene be produced in high yields, but also the resistance of the zeolite-containing catalyst to deactivation is high, so that the production of ethylene and propylene can be stably conducted for a prolonged period of time. In addition, by the method of the present invention, in the catalytic conversion of a hydrocarbon feedstock, it becomes possible to suppress the by-production of hydrogen, methane, ethane and aromatic hydrocarbons, and improve the selectivity for ethylene and propylene.

Further, the method of the present invention is advantageous in that there is no need to use a reactor system having a complicated system adapted for frequently regenerating the catalyst, and the desired ethylene and propylene can be produced using a simple reactor system, such as a fixed-bed, adiabatic reactor.

2. Prior Art

Various methods for the catalytic conversion of a hydrocarbon feedstock comprised of olefins, in which a zeolite-containing catalyst is employed, are conventionally known. In addition, a number of reports have been made on methods in which a zeolite-containing catalyst is used for producing ethylene and propylene from a hydrocarbon feedstock comprised of olefins by catalytic conversion.

However, for the below-mentioned reasons, it was difficult to stably produce ethylene and propylene efficiently from a hydrocarbon feedstock comprised of olefins by catalytic conversion for a prolonged period of time, using a zeolite-containing catalyst.

Both ethylene and propylene are intermediates of the reaction for converting olefins to aromatic hydrocarbons in the presence of a zeolite-containing catalyst, and these ethylene and propylene are converted to ultimate products, namely aromatic hydrocarbons, by successive conversion reaction.

Therefore, when it is intended to produce ethylene and propylene in high yields from a hydrocarbon feedstock comprised of olefins by catalytic conversion using a zeolite-containing catalyst, the activity of the catalyst and the reaction conditions must be strictly controlled. Illustratively stated, when the catalytic activity is too high and/or the time for contacting the hydrocarbon feedstock with the catalyst is too long, the produced ethylene and propylene are likely to be converted to ultimate aromatic hydrocarbons by successive reactions. On the other hand, when the catalytic activity is too low and/or the time for contacting the hydrocarbon feedstock with the catalyst is too short, the yields of ethylene and propylene are disadvantageously lowered.

Due to the high reactivity of olefins, deposition of carbonaceous material (coke) on the surface of a zeolite-containing catalyst (hereinafter, this deposition of coke is referred to as coking) is likely to occur during the catalytic conversion reaction of a hydrocarbon feedstock comprised of olefins. Therefore, when the conversion reaction is continuously performed, the catalyst is deactivated due to coking (hereinafter, this type of the deactivation of the catalyst is frequently referred to as "coking deactivation"), so that the catalytic activity is easily lowered.

In general, when a catalyst is deactivated by coking, the activity of the catalyst can be restored by heating the deactivated catalyst in the presence of oxygen-containing gas so that the coke accumulated on the catalyst is burnt off. However, when the regeneration operation is repeatedly conducted, the catalytic activity can no longer be satisfactorily restored. The reason why the catalytic activity can no longer be satisfactorily restored is as follows. In the above-mentioned regeneration operation, in which the coke accumulated on the zeolite catalyst is burnt off, steam is generated. When a zeolite is heated in the presence of the generated steam, the aluminum atoms in the zeolite, which are active sites of the zeolite, are eliminated from the crystal framework of the zeolite by hydrolysis reaction, so that the zeolite-containing catalyst is permanently deactivated (hereinafter, this type of the deactivation of the catalyst is frequently referred to as regeneration deactivations).

As mentioned above, especially when a catalytic conversion reaction of a hydrocarbon feedstock comprised of olefins is performed using a zeolite-containing catalyst, the catalyst is likely to suffer coking. In that case, it becomes necessary to frequently perform the above-mentioned regeneration operation and, therefore, the regeneration deactivation of the catalyst is most likely to occur.

Unexamined Japanese Patent Application Laid-Open Specification No. 49-41322 (corresponding to British Patent No. 1381427) discloses a method for converting paraffins, olefins and/or cycloparaffins (naphthenes), each having 5 or more carbon atoms, to aromatic hydrocarbons, ethylene and propylene, in which a proton form ZSM-5 zeolite is used as a catalyst. However, in this method, the yields of ethylene and propylene are low, whereas aromatic hydrocarbons are obtained in relatively high yields.

Unexamined Japanese Patent Application Laid-Open Specification No. 50-49233 (corresponding to British Patent No. 1394979) discloses a method for converting $C_2$–$C_4$ olefins and paraffins to aromatic hydrocarbons, ethylene and propylene, in which a proton form ZSM-5 zeolite is used as a catalyst. However, also in this method, the yields of ethylene and propylene are low, whereas aromatic hydrocarbons are produced in relatively high yields.

U.S. Pat. Nos. 4,527,001 and 4,613,721 disclose a method for converting butene to ethylene and propylene, in which an aluminophosphate molecular sieve is used. However, also in this method, the yields of ethylene and propylene are low.

Unexamined Japanese Patent Application Laid-Open Specification No. 3-27327 (corresponding to U.S. Pat. No. 5,043,522) discloses a method for producing ethylene and propylene, which comprises contacting a hydrocarbon feedstock comprised of a mixture of paraffins and olefins (each having 4 or more carbon atoms) with a proton form ZSM-5 zeolite as a catalyst, wherein the mixture has a specific composition. However, in this method, the conversion of the hydrocarbon feedstock is low, so that it is required to recycle a large amount of unreacted hydrocarbon feedstock.

Unexamined Japanese Patent Application Laid-Open Specification No. 6-73382 (corresponding to U.S. Pat. No. 5,171,921) discloses a method for converting $C_3$–$C_{20}$ hydrocarbons to ethylene and propylene, in which a specific proton form ZSM-5 zeolite containing phosphorus is used as a catalyst. However, in this method, with respect to the conversion reaction results in the case where only olefins are used as a feedstock, the performance of the catalyst is evaluated only in the initial stage of the conversion reaction, namely, 1 minute after the start of the feeding of the feedstock.

As a feature common to all of the above-mentioned conventional methods, there can be mentioned the use of a proton form zeolite as a catalyst. In general, a proton form zeolite has strong acidity, and such a catalyst is likely to cause successive conversion reactions of ethylene and propylene to form aromatic hydrocarbons. Thus, in all of the above-mentioned methods, it is difficult to improve the yields of ethylene and propylene. Further, when a hydrocarbon feedstock comprised of olefins is used, a proton form zeolite is likely to suffer not only coking deactivation but also regeneration deactivation.

International Patent Application publication No. WO96/13331 discloses a zeolite catalyst containing no proton, and a method for converting a hydrocarbon feedstock to ethylene, propylene and monocyclic aromatic hydrocarbons in presence of the zeolite catalyst containing no proton.

The catalyst used in this method is advantageous in that the regeneration deactivation of the catalyst is suppressed. However, the problem of occurrence of the coking deactivation of the catalyst remains unsolved. Therefore, when a hydrocarbon feedstock containing a large amount of olefins is used as a feedstock, the catalyst is likely to suffer coking deactivation.

Further, in this method, conversion reactions of paraffins occur simultaneously with the conversion reactions of olefins. For this reason, large amounts of various types of gases by-produced during the conversion reactions of paraffins (i.e., so-called "off gases"), such as hydrogen and methane, get mixed into the reaction mixture. Therefore, this method is disadvantageous in that the separation of ethylene and propylene from the reaction mixture is difficult.

In addition, the above-mentioned conversion reactions of paraffins are endothermic, so that it is required to supply the reactor with a large amount of heat. Therefore, in this method, a complicated, expensive reaction system is required.

SUMMARY OF THE INVENTION

In this situation, the present inventors have made extensive and intensive studies with a view toward developing a method for producing ethylene and propylene, which do not only suppress the coking deactivation and regeneration deactivation of the catalyst, which are problems inevitably accompanying the conventional methods for producing ethylene and propylene from a hydrocarbon feedstock by catalytic conversion using a zeolite-containing catalyst, but also makes it possible to efficiently and stably produce ethylene and propylene for a prolonged period of time. As a result, it has unexpectedly been found that, in the method for producing ethylene and propylene from a hydrocarbon feedstock by catalytic conversion, which comprises contacting, in a reactor, a hydrocarbon feedstock comprising at least one $C_4$–$C_{12}$ olefin with a zeolite-containing catalyst to thereby effect a catalytic conversion reaction of the at least one $C_4$–$C_{12}$ olefin, thereby obtaining a reaction mixture containing ethylene and propylene; and separating the ethylene and propylene from the reaction mixture, when a zeolite satisfying the below-mentioned specific requirements is used as a zeolite in a zeolite-containing catalyst, not only does it become possible to produce desired ethylene and propylene with high selectivity and in high yields, but also the coking deactivation and regeneration deactivation of the catalyst are suppressed, so that the production of the desired ethylene and propylene can be stably conducted for a prolonged period of time, even if the hydrocarbon feedstock comprises a high concentration (i.e., 20% by weight or more) of at least one $C_4$–$C_{12}$ olefin. In the method of the present invention, the zeolite in the zeolite-containing catalyst satisfies the following specific requirements:

(1) the zeolite is an intermediate pore size zeolite having a pore size of from 5 to 6.5 Å, (2) the zeolite contains substantially no proton, (3) the zeolite contains at least one metal selected from the group consisting of metals belonging to Group IB of the Periodic Table, and (4) the zeolite has an $SiO_2/Al_2O_3$ molar ratio of from 200 to 5,000.

The present invention has been completed, based on this novel finding.

Accordingly, it is primary object of the present invention to provide a method for stably and efficiently producing ethylene and propylene for a prolonged period of time, which makes it possible to suppress not only the coking deactivation but also the regeneration deactivation of the catalyst, which are problems inevitably accompanying the conventional methods for producing ethylene and propylene from a hydrocarbon feedstock containing olefins by catalytic conversion using a zeolite-containing catalyst.

The foregoing and other objects, features and advantages of the present invention will be apparent to those skilled in the art from the following detailed description and appended claims taken in connection with the accompanying drawing.

BRIEF DESCRIPTION OF THE DRAWING

In the accompanying drawing:

FIG. 1 is a flow sheet showing one mode of the method of the present invention for producing ethylene and propylene.

DETAILED DESCRIPTION OF THE INVENTION

According to the present invention, there is provided a method for producing ethylene and propylene from a hydrocarbon feedstock by catalytic conversion, which comprises:

contacting, in a reactor, a hydrocarbon feedstock comprising 20% by weight or more, based on the weight of the hydrocarbon feedstock, of at least one $C_4$–$C_{12}$ olefin with a zeolite-containing catalyst to thereby effect a catalytic conversion reaction of the at least one $C_4$–$C_{12}$ olefin, thereby obtaining a reaction mixture containing ethylene and propylene, wherein the zeolite in the zeolite-containing catalyst satisfies the following requirements (1), (2), (3) and (4):

(1) the zeolite is an intermediate pore size zeolite having a pore size of from 5 to 6.5 Å, (2) the zeolite contains substantially no proton, (3) the zeolite contains at least one metal selected from the group consisting of metals belonging to Group IB of the Periodic Table, and (4) the zeolite has an $SiO_2/Al_2O_3$ molar ratio of from 200 to 5,000; and separating the ethylene and propylene from the reaction mixture.

For easy understanding of the present invention, the essential feature and various embodiments of the present invention is enumerated below.

1. A method for producing ethylene and propylene from a hydrocarbon feedstock by catalytic conversion, which comprises:

contacting, in a reactor, a hydrocarbon feedstock comprising 20% by weight or more, based on the weight of the hydrocarbon feedstock, of at least one $C_4$–$C_{12}$ olefin with a zeolite-containing catalyst to thereby effect a catalytic conversion reaction of the at least one $C_4$–$C_{12}$ olefin, thereby obtaining a reaction mixture containing ethylene and propylene, wherein the zeolite in the zeolite-containing catalyst satisfies the following requirements (1), (2), (3) and (4):
   (1) the zeolite is an intermediate pore size zeolite having a pore size of from 5 to 6.5 Å,
   (2) the zeolite contains substantially no proton,
   (3) the zeolite contains at least one metal selected from the group consisting of metals belonging to Group IB of the Periodic Table, and
   (4) the zeolite has an $SiO_2/Al_2O_3$ molar ratio of from 200 to 5,000; and separating the ethylene and propylene from the reaction mixture.

2. The method according to item 1 above, wherein the separation of the ethylene and propylene from the reaction mixture is conducted by separating the reaction mixture into fraction A comprised mainly of hydrogen and hydrocarbons having 1 to 3 carbon atoms and fraction B comprised mainly of at least one hydrocarbon having 4 or more carbon atoms, followed by separation of the ethylene and propylene from fraction A.

3. The method according to item 2 above, which further comprises separating the fraction B into fraction $B_1$ comprised mainly of at least one hydrocarbon having 4 to 8 carbon atoms and fraction $B_2$ comprised mainly of at least one hydrocarbon having 9 or more carbon atoms, and recycling at least a part of the fraction $B_1$ to the reactor so as to use at least a part of the fraction $B_1$ as a part of the hydrocarbon feedstock.

4. The method according to item 2 above, wherein the fraction B is subjected to steam cracking to thereby obtain a steam cracking product containing ethylene and propylene, followed by separation of the ethylene and propylene from the steam cracking product.

5. The method according to any one of items 1 to 4 above, wherein the hydrocarbon feedstock comprises 50% by weight or more, based on the weight of the hydrocarbon feedstock, of at least one $C_4$–$C_{12}$ olefin.

6. The method according to any one of items 1 to 5 above, wherein the zeolite further contains at least one metal selected from the group consisting of alkali metals and alkaline earth metals.

7. The method according to any one of items 1 to 6 above, wherein, prior to the contacting with the hydrocarbon feedstock, the zeolite-containing catalyst is heated in the presence of steam at a temperature of 500° C. or more.

8. The method according to any one of items 1 to 7 above, wherein the at least one metal selected from the group consisting of metals belonging to Group IB of the Periodic Table is silver.

9. The method according to any one of items 1 to 8 above, wherein the zeolite is selected from the group consisting of zeolites belonging to the ZSM-5 zeolite family.

10. The method according to any one of items 1 to 9 above, wherein the catalytic conversion reaction of the at least one $C_4$–$C_{12}$ olefin is effected at a temperature of from 400 to 700° C. under a pressure of from 0.1 to 10 atm. and at a weight hourly space velocity of from 1 to 1000 $hr^{-1}$.

11. The method according to any one of items 1 to 9 above, wherein the catalytic conversion reaction of the at least one $C_4$–$C_{12}$ olefin is effected at a temperature of from 400 to 700° C. and at a weight hourly space velocity of from 1 to 1000 $hr^{-1}$, and wherein the hydrocarbon feedstock is a mixture thereof with a diluent gas, and the partial pressure of the hydrocarbon feedstock in the mixture is from 0.1 to 10 atm.

Hereinbelow, the present invention is described in detail.

In the method of the present invention, a hydrocarbon feedstock comprising 20% by weight or more, based on the weight of the hydrocarbon feedstock, of at least one $C_4$–$C_{12}$ olefin is used as a feedstock for producing ethylene and propylene.

In the present invention, the term "hydrocarbon feedstock" means a feedstock which is comprised mainly of at least one $C_1$–$C_{12}$ hydrocarbon, such as at least one member selected from the group consisting of a $C_1$–$C_{12}$ normal paraffin, an isoparaffin, an olefin, a cycloparaffin (naphthene) and a cycloparaffin having an alkyl side chain.

In the method of the present invention, the above-mentioned hydrocarbon feedstock comprises 20% by weight or more, based on the weight of the hydrocarbon feedstock, of at least one $C_4$–$C_{12}$ olefin. It should be noted that the term "olefin" mentioned above means cycloparaffins as well as straight chain, branched or cyclic olefins.

When the olefin content of the hydrocarbon feedstock is less than 20%, the yields of ethylene and propylene are unsatisfactory.

The content of at least one $C_4$–$C_{12}$ olefin in the above-mentioned hydrocarbon feedstock is preferably 30% by weight or more, more preferably 40% by weight or more, most preferably 50% by weight or more, based on the weight of the hydrocarbon feedstock.

The hydrocarbon feedstock may contain, as impurities, oxygen-containing compounds, such as tert-butanol, methanol and the like, in small amounts.

Examples of hydrocarbon feedstocks which can be preferably used in the present invention include:

(1) a $C_4$ fraction and a $C_5$ fraction, separated from a product obtained by subjecting a petroleum hydrocarbon, such as naphtha, to thermal cracking;

(2) a fraction obtained by removing a part or all of butadiene and isobutene from the $C_4$ fraction mentioned in item (1) above;

(3) a fraction obtained by removing a part or all of isoprene and cyclopentadiene from the $C_5$ fraction mentioned in item (1) above;

(4) a $C_4$ fraction and a gasoline fraction, separated from a product obtained by subjecting a petroleum hydrocarbon, such as a vacuum gas oil, to fluid catalyst cracking (FCC); and (5) a $C_4$ fraction and a gasoline fraction, separated from a coker.

These hydrocarbon feedstocks can be used individually or in combination.

In the method of the present invention, the above-mentioned hydrocarbon feedstock is contacted with a specific zeolite-containing catalyst to thereby effect a catalytic conversion reaction of the at least one $C_4$–$C_{12}$ olefin contained in the above-mentioned hydrocarbon feedstock, thereby obtaining a reaction mixture containing ethylene and propylene, and the ethylene and propylene are then separated from the reaction mixture.

In the method of the present invention, the above-mentioned zeolite in the zeolite-containing catalyst is a so-called "intermediate pore size zeolite" which is a zeolite having a pore size of from 5 to 6.5 Å. The term "Intermediate pore size zeolite" means a zeolite which has a pore size intermediate between the pore size of the small pore size zeolite (such as an A-type zeolite) and the pore size of the large pore size zeolite (such as a mordenite, an X-type zeolite and a Y-type zeolite), i.e., a zeolite containing 10-membered rings in the crystal framework thereof.

Examples of intermediate pore size zeolites include ZSM-5, ZSM-8, ZSM-11, ZSM-12, ZSM-21, ZSM-23, ZSM-35 and ZSM-38. Of these, zeolites of the ZSM-5 family, such as ZSM-5, ZSM-8 and ZSM-11; and ZSM-38 are preferred. In addition, the zeolites described in "*Stud. Surf. Sci. Catal.*" 33, pp. 167–215, written by P. A. Jacobs and J. A. Martens (published in the Netherlands, 1987), which are analogues of ZSM-5 and ZSM-11, can be used. Among the above-mentioned zeolites, ZSM-5 is most preferred.

In the present invention, a zeolite containing substantially no proton is used. The term "containing substantially no proton" means that a proton content (i.e, acid content) of the above-mentioned zeolite is 0.02 mmol or less per gram of zeolite, as measured by the liquid phase ion exchange/filtrate titration method explained below. Preferably, the proton content of the above-mentioned zeolite is 0.01 mmol or less per gram of zeolite.

The liquid phase ion exchange/filtrate titration method is described in *Intrazeolite Chemistry, "ACS Symp. Ser."* 218, pp. 369–382 (*U.S.A.*, 1983); *Nihon Kagakukaishi* (*Bulletin of the Chemical Society of Japan*), 3. pp. 521–527 (Japan, 1989) and the like. Measurement of the proton content is carried out as follows. A zeolite is calcined in air, and the calcined zeolite is subjected to an ion exchange treatment using an aqueous NaCl solution. Subsequently, the zeolite is collected by filtration, thereby obtaining an ion exchanged zeolite and a filtrate. The ion exchanged zeolite is washed with high purity water and the whole amount of the resultant washings are collected. The collected washings are mixed with the above-obtained filtrate to thereby obtain a solution mixture. The proton content of the obtained solution mixture is measured by neutralization titration, and the obtained value is defined as the proton content of the zeolite.

An ammonium ion-form zeolite and a multivalent metal cation-form zeolite (e.g., a rare earth metal cation-form zeolite) are known to generate protons by heating. Therefore, prior to the proton content measurement by the above-mentioned method, a zeolite should be calcined.

The above-mentioned zeolite used in the method of the present invention contains at least one metal selected from the group consisting of metals belonging to Group IB of the Periodic Table (hereinafter, frequently referred to as a "Group IB metals"), namely, at least one metal selected from the group consisting of copper, silver and gold. Of these metals, copper and silver are preferred, and silver is especially preferred.

The term "periodic table" means the periodic table described at pages 1 to 15 in *CRC Handbook of Chemistry and Physics* (75th Edition) written by David R. Lide et al. (published by CRC Press Inc., 1994–1995).

The term "zeolite containing a Group IB metal" means a zeolite containing a Group IB metal in the form of cations. However, in addition to the cations of Group IB metals, the zeolite may further contain Group IB metals in other forms, such as an oxide form.

As examples of methods for incorporating a Group IB metal into a zeolite, there can be mentioned a method in which a zeolite containing no Group IB metal is treated by a conventional method, such as an ion exchange method, an impregnation method and a kneading method. Among these methods, an ion exchange method is preferred.

When an ion-exchange method is used to incorporate a Group IB metal into a zeolite, a Group IB metal salt is used. Examples of Group IB metal salts include silver nitrate, silver acetate, silver sulfate, copper chloride, copper sulfate, copper nitrate and gold chloride.

There is no particular limitation with respect to the Group IB metal content of the zeolite, but preferably, the Group IB metal content is from 0.01 to 5% by weight, more preferably from 0.02 to 3% by weight, based on the weight of the zeolite. When the Group IB metal content of a zeolite in a zeolite-containing catalyst is less than 0.01% by weight, the catalytic activity of the catalyst is unsatisfactory. On the other hand, when the Group IB metal content of a zeolite in a zeolite-containing catalyst is more than 5% by weight, the catalyst usually shows no further improvement in the catalytic activity thereof.

The Group IB metal content of a zeolite can be measured by a conventional method, such as fluorescent X-ray analysis.

In the method of the present invention, it is required that the above-mentioned zeolite has an $SiO_2/Al_2O_3$ molar ratio of from 200 to 5,000. When the $SiO_2/Al_2O_3$ molar ratio of the zeolite in the zeolite-containing catalyst is less than 200, the catalyst is likely to be deactivated due to coking which occurs during the conversion reaction. On the other hand, when the $SiO_2/Al_2O_3$ molar ratio of a zeolite in a zeolite-containing catalyst is more than 5,000, the catalytic activity of the catalyst, becomes unsatisfactory.

The $SiO_2/Al_2O_3$ molar ratio of the zeolite is preferably 220 to 4.000, more preferably 250 to 3,500.

The $SiO_2/Al_2O_3$ molar ratio of the zeolite can be measured by a conventional method, for example, a method in which a zeolite is completely dissolved in an aqueous alkali solution and the resultant solution having dissolved therein the zeolite is analyzed by plasma emission spectrometry or the like.

In the method of the present invention, a metalloaluminosilicate in which some of the aluminum atoms of the zeolite framework are replaced by other metal atoms, such as Ga, Fe, B and Cr atoms, or a metallosilicate in which all of aluminum atoms of the zeolite framework are replaced by the above-mentioned metal atoms can also be used as the above-mentioned zeolite. In this case, the $SiO_2/Al_2O_3$ molar ratio of the zeolite is calculated as follows. Firstly, the content of the above-mentioned metal atoms of the metalloaluminosilicate or metallosilicate is converted to the number of moles of $Al_2O_3$, which is then added to the true number of moles of $Al_2O_3$ of the zeolite to thereby obtain an apparent number of moles of $Al_2O_3$ of the zeolite. Subsequently, using the apparent number of moles of $Al_2O_3$ of the zeolite, the $SiO_2/Al_2O_3$ molar ratio of the zeolite is calculated.

In addition, it is preferred that the above-mentioned zeolite further contains at least one metal selected from the group consisting of alkali metals and alkaline earth metals, more preferably at least one metal selected from the group consisting of alkali metals, most preferably at least one metal selected from the group consisting of sodium and potassium. In this case, the zeolite contains both a Group IB metal and at least one metal selected from the group consisting of alkali metals and alkaline earth metals.

As examples of methods for incorporating at least one metal selected from the group consisting of alkali metals and alkaline earth metals into a zeolite, substantially the same methods as described with respect to the incorporation of a Group IB metal into a zeolite can be mentioned.

The content of at least one metal selected from the group consisting of alkali metals and alkaline earth metals in the zeolite varies depending on the type of the metal. For example, when the metal is sodium, the sodium content is preferably 0.01 to 0.4% by weight, based on the weight of the zeolite. When the metal is potassium, the potassium content is preferably 0.01 to 0.8% by weight, based on the weight of the zeolite.

It is preferred that the zeolite contains at least one metal selected from the group consisting of alkali metals and alkaline earth metals in the form of cations.

With respect to the method for incorporating at least one metal selected from the group consisting of alkali metals and alkaline earth metals into the zeolite and the method for incorporating a Group IB metal into the zeolite, there is no particular limitation on the order and number of times of conducting these methods. For example, at least one metal selected from the group consisting of alkali metals and alkaline earth metals can be incorporated into a zeolite before a Group IB metal is incorporated into the zeolite. Alternatively, a Group IB metal can be incorporated into a zeolite before at least one metal selected from the group consisting of alkali metals and alkaline earth metals is incorporated into the zeolite.

However, in both cases, it is required that the resultant metal-containing zeolite contains substantially no proton.

If desired, in order to suppress the coking deactivation of a zeolite and/or to improve the yields of ethylene and propylene, the above-mentioned zeolite-containing catalyst may further contain at least one metal selected from the group consisting of metals belonging to Groups IIB, III, VB, VIB, VIIB and VIII of the periodic table, such as V, Cr, Mo, W, Mn, Pt, Pd, Fe, Ni, Zn and Ga. The method for incorporating these metals into a zeolite is substantially the same as the method for incorporating a Group IB metal into a zeolite, except for the type of metals to be incorporated. It is preferred that the content of these metals of the zeolite is from 0.1 to 2% by weight, based on the weight of the zeolite.

If desired, in order to further improve the resistance of the zeolite to the coking deactivation, prior to the contact with the hydrocarbon feedstock, the above-mentioned zeolite can be subjected to heat treatment at 500° C. or more in the presence of steam. Preferably, this heat treatment (steaming) is conducted at 500° C. to 900° C. under a steam partial pressure of 0.01 atm or more.

The above-mentioned heat treatment can be conducted before a Group IB metal is incorporated into the zeolite, but it is preferred that the heat treatment is conducted after a Group IB metal is incorporated into the zeolite.

When the zeolite-containing catalyst is used for a catalytic conversion reaction for a long time, the catalyst may suffer coking deactivation. The deactivated catalyst can be subjected to treatment for regeneration, wherein this treatment consists in burning off the coke accumulated on the catalyst at a temperature of from 400 to 700° C. usually in an atmosphere of air or a gaseous mixture of oxygen and an inert gas (hereinafter, this treatment is frequently referred to as a "regeneration treatment").

As mentioned above, during the regeneration treatment, steam is generated. The generated steam can be used for conducting the above-mentioned heat treatment (steaming) for improving the resistance of a zeolite-containing catalyst to the coking deactivation. That is, substantially the same effect as that achieved by subjecting the catalyst to the above-mentioned heat treatment (steaming) can be achieved by repeatedly performing a sequence of the catalytic conversion of a hydrocarbon feedstock using a zeolite for a long time and the regeneration treatment of the coked catalyst.

If desired, the zeolite can be calcined prior to be used as a catalyst. Usually, the zeolite is calcined at 500 to 900° C.

It is preferred that prior to the use of the zeolite-containing catalyst, the catalyst is shaped to particles. When the catalyst is shaped, the above-mentioned zeolite alone may be shaped, and used as the zeolite-containing catalyst. However, usually, the above-mentioned zeolite is mixed with a porous material of refractory inorganic oxide, such as alumina, silica, silica/alumina, zirconia, titania, diatomaceous earth, clay and the like (as a binder or a diluent for shaping (a matrix)), and the resultant mixture is shaped for use as the zeolite-containing catalyst.

When a matrix or binder is used, it is preferred that the content of the matrix or binder is in the range of from 10 to 90% by weight, more preferably from 20 to 50% by weight, based on the total weight of the zeolite and the matrix or binder.

In the present invention, by virtue of the use of the zeolite-containing catalyst as specified above, the occurrence of the coking deactivation accompanying the conventional methods is suppressed, even if a hydrocarbon feedstock containing an olefin in a concentration as high as 20% by weight or more is used, and thus, there is no need to frequently repeat the regeneration operation. As a result, it has become possible to stably, effectively produce the desired ethylene and propylene for a prolonged period of time.

In the present invention, a hydrocarbon feedstock comprising at least one $C_4$–$C_{12}$ olefin is contacted with the zeolite-containing catalyst to thereby effect a catalytic conversion reaction of the $C_4$–$C_{12}$ olefin. It is preferred that the catalytic conversion reaction of the $C_4$–$C_{12}$ olefin is effected under reaction conditions described below, in which not only is the $C_4$–$C_{12}$ olefin in the hydrocarbon feedstock converted to ethylene and propylene with high selectivity, but also substantially no reaction of paraffins coexisting in the hydrocarbon feedstock occurs. The reaction temperature Is preferably of from 400 to 700° C., more preferably from 500 to 650° C. With respect to the reaction pressure, a low pressure is preferred. The reaction pressure is generally from 0.1 to 10 atm, preferably from 0.2 to 8 atm. The weight hourly space velocity (WHSV) of the hydrocarbon feedstock is preferably from 1 to 1,000 $hr^{-1}$, more preferably from 5 to 500 $hr^{-1}$, based on the weight of the zeolite in the zeolite-containing catalyst. The time for contacting the hydrocarbon feedstock with the zeolite-containing catalyst is preferably 5 seconds or less, more preferably 1 second or less.

The above-mentioned hydrocarbon feedstock may be a mixture thereof with a dilution gas. When a mixture of a hydrocarbon feedstock and a dilution gas is used, a low partial pressure of the hydrocarbon feedstock is preferred. The partial pressure of the hydrocarbon feedstock Is generally from 0.1 to 10 atm preferably from 0.2 to 8 atm. Examples of dilution gases include hydrogen, methane, steam and an inert gas, such as nitrogen.

When hydrogen is used as a dilution gas, it is preferred that the molar ratio of the hydrocarbon feed-stock to the hydrogen is in the range of from 0.01 to 1.

When the catalytic conversion reaction is conducted under the above-mentioned conditions wherein substantially no reaction of paraffins in the hydrocarbon feedstock occurs, the conversion reaction of the olefin in the hydrocarbon feedstock is selectively promoted whereas the conversion reaction of the paraffin is suppressed. As a result, by-production of methane, ethane, propane and the like due to the conversion reactions of paraffins is suppressed, and thus, the separation and purification of ethylene and propylene from the reaction mixture become easy.

In the method of the present invention, any type of reactor selected from the group consisting of a fixed-bed reactor, a moving-bed reactor, a fluidized-bed reactor and a transfer line reactor can be used as a reactor for contacting a hydrocarbon feedstock with a zeolite-containing catalyst.

Deactivation of the zeolite-containing catalyst used in the method of the present invention due to coking is unlikely to occur, so that ethylene and propylene can be stably produced for a prolonged period of time, even if a fixed-bed reactor is employed.

The conversion reaction of a paraffin is highly endothermic, whereas the conversion reaction of an olefin is slightly endothermic or exothermic, depending on the reaction conditions. When olefins in the hydrocarbon feedstock are selectively reacted under the above-mentioned conditions wherein substantially no reaction of paraffins in the hydrocarbon feedstock occurs, the amount of heat absorbed during the conversion reactions of paraffins becomes relatively small (depending on the reaction conditions used, it is possible that the amount of heat generated during the conversion reaction of olefins slightly exceeds the amount of heat absorbed during the conversion reactions of paraffins, so that, as a whole, the reaction becomes exothermic). Therefore, in the method of the present invention, it is not necessary to supply a large amount of reaction heat, so that a simple reactor system, such as a fixed-bed, single-stage adiabatic reactor, can be used.

The reaction mixture obtained by the catalytic conversion reaction of the hydrocarbon feedstock contains ethylene and propylene, and the ethylene and propylene are separated from the reaction mixture. It is preferred that the separation of ethylene and propylene from the reaction mixture is conducted in such a manner that the reaction mixture is separated into fraction A comprised mainly of hydrogen and hydrocarbons having 1 to 3 carbon atoms and fraction B comprised mainly of at least one hydrocarbon having 4 or more carbon atoms, followed by separation of the ethylene and propylene from fraction A. This separation process can be performed by using various conventional methods in combination, such as distillation, extraction and the like.

Usually, the above-mentioned reaction mixture contains $C_4$–$C_8$ olefins, as well as ethylene and propylene. Therefore, when a so-called "recycle system", wherein all or a part of the $C_4$–$C_8$ olefins are separated from the reaction mixture and recycled to the reactor, is employed for the production of ethylene and propylene, the hydrocarbon feedstock can be efficiently utilized.

Illustratively stated, it is preferred that the above-mentioned fraction B is separated into fraction $B_1$ comprised mainly of at least one $C_4$–$C_8$ hydrocarbon and fraction $B_2$ comprised mainly of at least one hydrocarbon having 9 or more carbon atoms, and at least a part of fraction $B_1$ is recycled to the reactor so as to use the at least a part of fraction $B_1$ as a part of the hydrocarbon feedstock.

Hereinbelow, the recycle system for producing ethylene and propylene is described in more detail, referring to a specific example wherein a $C_4$ fraction (a fraction comprised mainly of $C_4$ hydrocarbons, such as butane, isobutane, butene, and isobutene) obtained from a steam cracking product of a petroleum hydrocarbon is used as a hydrocarbon feedstock.

FIG. 1 is a flow sheet showing one preferred mode of the recycle system using a $C_4$ fraction as a hydrocarbon feedstock.

First, a reaction mixture (comprising hydrogen and hydrocarbons having one or more carbon atoms) is separated into a fraction comprised mainly of hydrogen and $C_1$–$C_3$ hydrocarbons (hereinafter, simply referred to as a "$H_2$–$C_3$ fraction") and a fraction comprised mainly of at least one hydrocarbon having 4 or more carbon atoms (hereinafter, simply referred to as a "$C_4^+$ fraction"). With respect to the apparatus used for the separation (i.e., a $C_3$ separator), a distillation tower, a flash drum (a gas-liquid separator) and the like can be used.

Ethylene and propylene are collected from the obtained $H_2$–$C_3$ fraction.

Next, the above-mentioned $C_4^+$ fraction is separated into a fraction comprised mainly of $C_4$ hydrocarbons (hereinafter, simply referred to as a "$C_4$ fractions") and a fraction comprised mainly of at least one hydrocarbon having 5 or more carbon atoms (hereinafter, simply referred to as a "$C_5^+$ fraction"). With respect to the apparatus used for the separation (i.e., a $C_4$ separator), a distillation tower, a flash drum (a gas-liquid separator) and the like can be used.

Further, the above-mentioned $C_5^+$ fraction is separated into a fraction comprised mainly of at least one $C_5$–$C_8$ hydrocarbon (hereinafter, simply referred to as a "$C_5$–$C_8$ fraction") and a fraction comprised mainly of at least one hydrocarbon having 9 or more carbon atoms (i.e., "a fraction having a boiling point higher than that of $C_8$ aromatics" indicated in FIG. 1). With respect to the apparatuses used for the separation (i.e., a $C_8$ separator), a distillation tower, a flash drum (a gas-liquid separator) and the like can be used.

The obtained $C_4$ fraction and $C_5$–$C_8$ fraction are mixed together to thereby obtain a fraction comprising at least one hydrocarbon having 4 to 8 carbon atoms (hereinafter, simply referred to as a "$C_4$–$C_8$ fraction"). The obtained $C_4$–$C_8$ fraction is recycled to the reactor and used as a part of the hydrocarbon feedstock.

In the recycle system, butane contained in the hydrocarbon feedstock is concentrated in the $C_4$ fraction separated by means of the above-mentioned $C_4$ separator. For this reason, if all of the $C_4$ fraction is recycled to the reactor, the butane concentration of the hydrocarbon feedstock charged into the reactor would become high, so that the concentration of at least one olefin having 4 to 12 carbons in the hydrocarbon feedstock may become unsatisfactory. Therefore, it is preferred that only a part of the $C_4$ fraction is recycled to the reactor so as to suppress the increase in the butane concentration of the feedstock.

In FIG. 1, each of $C_3$ separator, $C_4$ separator and $C_8$ separator is shown in independent form, but the number and order of separators in the recycling reaction system are not limited to those shown in FIG. 1 and may be appropriately varied.

In addition, aromatic hydrocarbons can be collected from the fraction having a boiling point higher than that of $C_8$ aromatics.

In the method of the present invention, when the production of ethylene and propylene by catalytic conversion is conducted simultaneously with the production of ethylene and propylene by steam cracking (coil pyrolysis), the yields of ethylene and propylene, per weight of the hydrocarbon feedstock, can be improved. In that case, the by-production of methane and the like can be suppressed, so that the purification of ethylene and propylene can be efficiently performed.

As an example of such a method, there can be mentioned a method in which the above-mentioned fraction B is charged into a coil pyrolysis furnace, the fraction B is subjected to steam cracking to thereby obtain a steam cracking product containing ethylene and propylene and the ethylene and propylene are separated from the obtained steam cracking product.

In that case, it is preferred that the steam cracking is conducted under conditions wherein the temperature in the pyrolysis coil is from 750 to 850° C., the pressure in the pyrolysis coil is from 0 to 15 kg/cm²·G, the residence time is from 0.1 to 0.8 second, and the steam/hydrocarbon weight ratio is from 0.1 to 1.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, various properties of zeolites are measured by the following methods.

(1) Measurement of the amount of Protons in a Zeolite by the Liquid Phase ion Exchange/Filtrate Titration Method 1.5 g of a zeolite is calcined at 400 to 600° C. in air, and subjected to ion exchange treatment in 25 ml of a 3.4 mol/liter aqueous NaCl solution for 10 minutes under ice-cooling conditions. The resultant mixture containing the zeolite is filtered so that the zeolite is separated from a filtrate, and the separated zeolite is washed with 50 ml of pure water on the filter. The whole amount of the filtrate (including the water used for the washing of the separated zeolite) is recovered, and analyzed by neutralization titration with a 0.1 N aqueous NaOH solution so as to determine the point of neutralization, and the amount of protons in the zeolite is calculated from the point of neutralization.

(2) Measurement of the $SiO_2/Al_2O_3$ Molar Ratio of a Zeolite

To 50 g of a 5 N aqueous NaOH solution is added 0.2 g of a zeolite. The resultant mixture is transferred to a stainless microbomb having a Teflon inner tube, and the microbomb is hermetically sealed. The microbomb is heated in an oil bath maintained at a temperature of 150° C. for 12 to 70 hours to thereby completely dissolve the zeolite in the NaOH solution. The resultant solution having dissolved therein the zeolite is diluted with ion-exchanged water. (The degree of dilution suitable for the below-mentioned measurement by using an inductively coupled plasma emission spectrometer (hereinbelow, referred to as "ICP spectrometerm") varies depending on the composition of the zeolite or the like. The above-obtained solution having dissolved therein the zeolite is diluted in approximately 5- to 100- fold so as to be suitable for the below-mentioned measurement by ICP.) The concentrations of silicon and aluminum are measured by ICP using the below-mentioned ICP spectrometer under the below-mentioned conditions, and the $SiO_2/Al_2O_3$ molar ratio of the zeolite is calculated from the concentrations of silicon and aluminum.

ICP spectrometer and conditions for ICP spectrometry are as follows:

ICP spectrometer

JOBIN YVON(JY138 ULTRACE) (manufactured and sold by Rigaku Corporation, Japan)

Conditions for ICP

Wavelength for measuring the concentration of silica: 251.60 nm

Wavelength for measuring the concentration of aluminum: 396.152 nm

Plasma power: 1.0 kW

Flow rate of the nebulizer gas: 0.28 1/min

Flow rate of the sheath gas: 0.3 to 0.8 1/min

Flow rate of the coolant gas: 13 1/min

The reaction rate constant K, which is an index of catalytic activity of the catalyst, is calculated by the following formula:

Reaction rate=$WHSV \times \ln(1/(1-X))$; constant $K$ wherein WHSV means the weight hourly space velocity, and X represents the conversion of butenes in the feedstock material which is defined by the following formula:

$$\text{Conversion } X \text{ of butenes in the feedstock material} = \frac{\text{Butenes concentration of the feedstock material} - \text{Butenes concentration of the product}}{\text{Butenes concentration of the feedstock material}}.$$

EXAMPLE 1

A $Na^+$ form ZSM-5 zeolite having a $SiO_2/Al_2O_3$ molar ratio of 300 is dispersed in a 0.05 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120 C. for 5 hours, followed by calcination in air at 550° C., thereby obtaining Catalyst A. The Ag content and $Ag_2O/Na_2O$ molar ratio of Catalyst A are measured by fluorescent X-ray analysis. The Ag content is 1.0% by weight. The $Ag_2O/Na_2O$ molar ratio is 0.82/0.18. The fluorescent X-ray analysis is conducted by means of X-ray SPECTROMETER RIX 3000 (manufactured and sold by Rigaku Corporation, Japan), using a sample obtained by compression molding a zeolite which is 4-fold diluted with Avicel (crystalline cellulose manufactured and sold by Asahi Kasei Kogyo Kabushiki Kaisha, Japan). The amount of protons in Catalyst A measured by the liquid phase ion exchange/filtrate titration method is 0.002 mmol/g.

Catalyst A is compression molded and pulverized. The resultant particles are sieved to collect those having a particle size of from 22 to 30 mesh. 0.36 g of the collected Catalyst A is diluted with 1.14 g of pulverized Raschig rings (made of porcelain) having the same particle size as mentioned above, i.e., 22 to 30 mesh, and charged into a quartz glass reactor having an inner diameter of 16 mmϕ. Nitrogen gas is charged into and flowed through the reactor at a flow rate of 100 cc/min under atmospheric pressure, and the temperature is elevated to a predetermined temperature (approximately 600° C.) by means of a tubular electric furnace. Subsequently, in place of the nitrogen gas, a $C_4$ raffinate-2 (obtained by extracting butadiene and isobutene from a $C_4$ fraction obtained by the steam cracking of naphtha) is charged into the reactor at a flow rate of 15 g/hr. The reaction is continuously performed for 48 hours under conditions wherein the reaction temperature is 600° C. and WHSV (weight hourly space velocity)=41.7 ($hr^{-1}$). The compositions of the resultant reaction products, obtained at predetermined points in time after the start of the feeding of the feedstock material (shown in Table 2), are analyzed by directly introducing a portion of each of the respective reaction products into a gas chromatograph (using a thermal conductivity detector (TCD) and a flame ionization detector (FID)). The analysis by gas chromatography is performed under the following conditions:

Chromatograph: GC-17A type gas chromatograph (manufactured and sold by Shimadzu Corporation, Japan);

Column: Custom capillary column SPB-1 (inner diameter: 0.25 mm, length: 60 m, thickness of film: 3.0 $\mu$m) (manufactured and sold by Supelco Corporation, U.S.A.);

Amount of the sample gas: 1 ml (the temperature of the sampling line is maintained at 200 to 300° C. in order to prevent liquefaction.);

Temperature elevation program, wherein the column temperature is maintained at 40° C. for 12 minutes, elevated to 200° C. with a temperature elevation rate of 5° C./min, and maintained at 200° C. for 22 minutes;

Split ratio: 200:1;

Flow rate of the carrier gas (nitrogen gas): 120 ml/min;

Operation conditions of FID detector, wherein:
pressure of air charged: 50 kPa (approximately 500 ml/min), and
pressure of hydrogen charged: 60 kPa (approximately 50 ml/min); and Method of the operation for the measurement, wherein: the TCD and FID are connected in series, where-upon hydrogen and hydrocarbons each having 1 to 2 carbon atoms are detected by the TCD, whereas hydrocarbons each having 3 or more carbon atoms are detected by the FID (the detection by the TCD is switched to the detection by the FID 10 minutes after the start of the analysis).

The results are shown in Table 2. The reaction rate constant K at 30 minutes after the start of the reaction is 54.6 ($hr^{-1}$).

Comparative Example 1

The conversion reaction of a $C_4$ raffinate-2 is conducted under substantially the same conditions as in Example 1, except that a $H^+$ form ZSM-5 zeolite having a $SiO_2/Al_2O_3$ molar ratio of 300 is used as a catalyst and that the reaction is terminated 24 hours after the start of the reaction since the deactivation of the catalyst is rapid. The results are shown in Table 3.

The reaction rate constant K at 30 minutes after the start of the reaction is 44.9 ($hr^{-1}$).

Comparison between Tables 2 and 3 clearly shows that when catalyst A as prepared and used in Example 1 is used, the yields of propylene and ethylene in the initial stage of the reaction is high, and that the yield lowering in Example 1 with the lapse of time is extremely small, as compared to that in Comparative Example 1.

EXAMPLE 2

4 g of Catalyst A as used in Example 1 is charged into a quartz glass reactor having an inner diameter of 16 mm$\phi$, and steamed for 5 hours under conditions wherein the temperature is 650° C., the flow rate of steam is 27.6 g/hr and the flow rate of nitrogen gas is 140 Ncc/min (cc/min. under normal temperature and pressure conditions, i.e., 0° C. and 1 atm.). The amount of protons in Catalyst A after steaming, which is measured by the liquid phase ion exchange/filtrate titration method, is 0.002 mmol/g. 0.6 g of Catalyst A after steaming is diluted with 0.9 g of pulverized Raschig rings (made of porcelain) and charged into the reactor. The conversion reaction of a $C_4$ raffinate-2 is conducted under substantially the same conditions as in Example 1, except that the amount of the $C_4$ raffinate-2 charged into the reactor is 22.5 g/hr (WHSV=37.5 $hr^{-1}$). The results are shown in Table 4. The reaction rate constant K at 30 minutes after the start of the reaction is 51.9 ($hr^{-1}$). After completion of the 48-hour reaction, nitrogen gas is charged into the reactor, thereby purging the hydrocarbon in the reactor. Then, the temperature of the catalyst layer is maintained at 500° C. Subsequently, air/nitrogen gas (oxygen concentration is 2% by volume) is charged into and flowed through the reactor, so that the coke accumulated on the catalyst is burnt off. A portion of the gas discharged from the outlet of the reactor (hereinbelow, this discharged gas is referred to as "regeneration gas") is periodically taken as a sample, and analyzed by gas chromatography for measuring the concentrations of $CO_2$ and CO in the regeneration gas. The amount of coke is calculated from the concentrations of $CO_2$ and CO.

The analysis of the regeneration gas by gas chromatography is performed under the following conditions: Chromatograph: GC-8A type gas chromatograph (manufactured and sold by Shimadzu Corporation, Japan) with a thermal conductivity detector (TCD) Column: the following Columns (1) and (2) are connected in parallel:

Column (1): a SUS column having an inner diameter of 3 mm and a length of 3 m, which is packed with Molecular Sieve 5A (80 to 100 mesh, manufactured and sold by Wako Pure Chemical Industries, Ltd., Japan), and Column (2): a SUS column having an inner diameter of 3 mm and a length of 2 m, which is packed with Porapac-Q (80 to 100 mesh, manufactured and sold by WATERS ASSOCIATES Co., Ltd., U.S.A.) and which is connected, in series, to a SUS column having an inner diameter of 3 mm and a length of 1 m;

Carrier gas: helium gas (flow rate: 60 ml/min); and Column temperature: 70° C.

The yield of the coke obtained by dividing the amount of the coke with the total amount of the feed-stock material charged into the reactor is found to be 74 ppm by weight.

As apparent from comparison between Tables 4 and 2, as a result of the steaming, the catalytic activity of the zeolite is slightly lowered, but the deactivation of the zeolite is further suppressed.

Comparative Example 2

The $H^+$ form ZSM-5 zeolite as used in Comparative Example 1, which has an $SiO_2/Al_2O_3$ molar ratio of 300, is subjected to steaming under substantially the same conditions as in Example 2, and the conversion reaction of a $C_4$ raffinate-2 is conducted under substantially the same conditions as in Example 2, except that WHSV is 16.7 ($hr^{-1}$). The yields (% by weight) at 30 minutes after the start of the reaction are as follows.

Hydrogen+methane: 2.1%,
Ethylene: 12.7%,
Ethane: 0.7%,
Propylene: 27.9%,
Propane: 1.9%,
Butenes: 16.7%,
Butanes: 21.7%,
$C_5$–$C_8$ PNO (paraffins, naphthenes and olefins each having 5 to 8 carbon atoms): 8.2%, $C_6$–$C_8$ A (aromatic hydrocarbons each having 6 to 8 carbon atoms): 7.6%, and $C_9$+ (hydrocarbons each having 9 or more carbon atoms): 0.5%.

Further, the yields (% by weight) at 48 hours after the start of the reaction are as follows.

Hydrogen+methane: 0.6%,

Ethylene: 6.4%,

Ethane: 0.3%,

Propylene: 25.9%,

Propane: 0.7%

Butenes: 30.2%,

Butanes: 21.7%, $C_5$–$C_8$ PNO: 11.6%

$C_6$–$C_8$ A: 2.5%, and $C_9$+:0.1%.

The reaction rate constant K at 30 minutes after the start of the reaction is 21.1 ($hr^{-1}$). After completion of the reaction, the catalyst is regenerated by substantially the same method as in Example 2, and the amount of coke is measured. The yield of the coke is 208 ppm by weight.

Comparison between the results of Example 2 and those of Comparative Example 2 shows that, surprisingly, despite that the catalytic activity of the catalyst used in the method of the present invention Is high, as compared to that of the conventional proton form zeolite catalyst used in Comparative Example 2, the amount of the coke generated during the reaction performed by the method of the present invention is extremely small, as compared to the amount of the coke generated during the reaction performed in Comparative Example 2.

It is known that when a zeolite catalyst is steamed at a high temperature, the zeolite catalyst suffers permanent deactivation. In the operation for the regeneration of a zeolite catalyst, in which the coke accumulated on the zeolite catalyst is burnt off, steam is generated due to the burning of hydrogen gas contained in the coke. As a result, when the operation for the regeneration of a zeolite catalyst is repeatedly conducted, deactivation of the zeolite catalyst occurs (regeneration deactivation). Therefore, the resistance of the zeolite catalyst to the regeneration deactivation can be evaluated, based on the change in the catalytic activity caused by the steaming. In order to evaluate the resistance to the regeneration deactivation with respect to the zeolite catalyst used in the present invention, comparison is made with respect to the reaction rate constants in Examples 1 and 2, and Comparative Examples 1 and 2. The results are shown in Table 15. As apparent from Table 15, the deactivation of the catalyst used in the method of the present invention is extremely small, and this clearly shows that the resistance of the catalyst used in the method of the present invention to the regeneration deactivation is very high.

EXAMPLE 3

A Na+ form ZSM-5 zeolite having a $SiO_2/Al_2O_3$ molar ratio of 230 is dispersed in a 0.015 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Catalyst B. The Ag content and $Ag_2O/Na_2O$ molar ratio of Catalyst B are measured by fluorescent X-ray analysis. The Ag content is 1.0% by weight. The $Ag_2O/Na_2O$ molar ratio is 0.66/0.34. 4 g of Catalyst B is charged into a quartz glass reactor having an inner diameter of 16 mmφ, and steamed for 5 hours under conditions wherein the temperature is 650° C., the flow rate of steam is 27.6 g/hr and the flow rate of nitrogen gas is 140 Ncc/min. The amount of protons in Catalyst B after steaming, which is measured by the liquid phase ion exchange/filtrate titration method, is 0.002 mmol/g. 0.6 g of Catalyst B after steaming is diluted with 0.9 g of pulverized Raschig rings (made of porcelain) and charged into the reactor. The conversion reaction of a $C_4$ raffinate-2 is conducted under substantially the same conditions as in Example 2, except that the reaction time is 24 hours. The results are shown in Table 5.

Comparative Example 3

A $Na^+$ form ZSM-5 zeolite having a $SiO_2/Al_2O_3$ molar ratio of 86 is dispersed in a 0.015 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Comparative Catalyst A'. The Ag content and $Ag_2O/Na_2O$ molar ratio of Comparative Catalyst A' are measured by fluorescent X-ray analysis. The Ag content is 1.1% by weight. The $Ag_2O/Na_2O$ molar ratio is 0.28/0.72. 4 g of Comparative Catalyst A' is charged into a quartz glass reactor having an inner diameter of 16 mmφ, and steamed for 5 hours under conditions wherein the temperature is 650° C., the flow rate of steam is 27.6 g/hr and the flow rate of nitrogen gas is 140 Ncc/min. The amount of protons in Comparative Catalyst A' after steaming, which is measured by the liquid phase ion exchange/filtrate titration method, is 0.003 mmol/g. 0.36 g of Comparative Catalyst A' after steaming is diluted with 1.14 g of pulverized Raschig rings (made of porcelain) and charged into the reactor. The conversion reaction of a $C_4$ raffinate-2 is conducted under substantially the same conditions as in Example 1, except that the reaction time is 24 hours. The results are shown in Table 6.

Comparative Example 4

A $Na^+$ form ZSM-5 zeolite having a $SiO_2/Al_2O_3$ molar ratio of 175 is dispersed in a 0.01 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Comparative Catalyst B'. The Ag content and $Ag_2O/Na_2O$ ratio of Comparative Catalyst B' are measured by fluorescent X-ray analysis. The Ag content is 0.9% by weight. The $Ag_2O/Na_2O$ molar ratio is 0.45/0.55. 4 g of Comparative Catalyst B' is charged into a quartz glass reactor having an inner diameter of 16 mmφ, and steamed for 5 hours under conditions wherein the temperature is 650° C., the flow rate of steam is 27.6 g/hr and the flow rate of nitrogen gas is 140 Ncc/min. The amount of protons in Comparative Catalyst B' after steaming, which is measured by the liquid phase ion exchange/filtrate titration method, is 0.002 mmol/g. 0.85 g of Comparative Catalyst B' after steaming is diluted with 0.65 g of pulverized Raschig rings (made of porcelain) and charged into the reactor having an inner diameter of 16 mmφ. The conversion reaction of a $C_4$ raffinate-2 is conducted under substantially the same conditions as in Example 1, except that the reaction time is 24 hours. The results are shown in Table 7.

Comparison of Tables 4 and 5 with Tables 6 and 7 clearly shows that the effect of the $SiO_2/Al_2O_3$ molar ratio of a zeolite on the deactivation of the catalyst is extremely large, and that when the zeolite having a high $SiO_2/Al_2O_3$ molar ratio is used, the catalytic activity of the catalyst is stable for a prolonged period of time.

EXAMPLE 4

0.8 g of Catalyst A is diluted with 0.7 g of pulverized Raschig rings (made of porcelain) and charged into a quartz glass reactor having an inner diameter of 16 mm$\phi$.

The conversion reaction is conducted using 1-hexene as a feedstock material under conditions wherein the reaction temperature is 550° C., the amount of 1-hexene charged into the reactor is 74.5 g/hr (WHSV=93 hr$^{-1}$), the flow rate of nitrogen gas is 75 Ncc/min and the pressure is atmospheric pressure. The gas discharged from the outlet of the reactor (hereinbelow, referred to as "reaction gas") 30 minutes after the start of the feeding of the feedstock material is analyzed. The results are shown in Table 8.

EXAMPLE 5

A $Na^+$ form ZSM-5 zeolite having a $SiO_2/Al_2O_3$ molar ratio of 300 is dispersed in a 0.005 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Catalyst C. The Ag content and $Ag_2O/Na_2O$ molar ratio of Catalyst C are measured by fluorescent X-ray analysis. The Ag content is 0.4% by weight. The $Ag_2O/Na_2O$ molar ratio is 0.34/0.66. 4 g of Catalyst C is charged into a quartz glass reactor having an inner diameter of 16 mm$\phi$, and steamed for 5 hours under conditions wherein the temperature is 650° C., the flow rate of steam is 27.6 g/hr and the flow rate of nitrogen gas is 140 Ncc/min. The amount of protons in Catalyst C after steaming, which is measured by the liquid phase ion exchange/filtrate titration method, is 0.002 mmol/g. 1.75 g of Catalyst C after steaming is charged into the reactor having an inner diameter of 16 mm$\phi$. The conversion reaction is conducted using 1-butene as a feedstock material under conditions wherein the reaction temperature is 600° C., the amount of 1-butene charged into the reactor is 16.6 g/ hr (WHSV=9.5 hr$^{-1}$) and the pressure is atmospheric pressure. The reaction gas at 30 minutes after the start of the feeding of the feedstock material is analyzed. The results are shown in Table 8.

EXAMPLE 6

A $Na^+$ form ZSM-5 zeolite having a $SiO_2/Al_2O_3$ molar ratio of 300 is dispersed in an aqueous solution containing a mixture of silver nitrate and potassium nitrate (concentration of silver nitrate: 0.006 N, concentration of potassium nitrate: 0.003 N) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Catalyst D. The Ag content, K content and $Ag_2O/Na_2O/K_2O$ molar ratio of Catalyst D are measured by fluorescent X-ray analysis. The Ag content is 0.4% by weight. The K content is 0.1% by weight. The $Ag_2O/Na_2O/K_2O$ molar ratio is 0.34/0.43/0.23. 4 g of Catalyst D is charged into a quartz glass reactor having an inner diameter of 16 mm$\phi$, and steamed for 5 hours under conditions wherein the temperature is 650° C., the flow rate of steam is 27.6 g/hr and the flow rate of nitrogen gas is 140 Ncc/min. The amount of protons in Catalyst D after steaming, which is measured by the liquid phase ion exchange/filtrate titration method, is 0.002 mmol/g. 1.75 g of Catalyst D after steaming is charged into the reactor having an inner diameter of 16 mm$\phi$. The conversion reaction is conducted using 1-butene as a feedstock material under conditions wherein the reaction temperature is 600° C., the amount of 1-butene charged into the reactor is 17.8 g/hr (WHSV=10.2 hr$^{-1}$) and the pressure is atmospheric pressure. The reaction gas at 30 minutes after the start of the feeding of the feedstock material is analyzed. The results are shown in Table 8.

EXAMPLE 7

3 g of Catalyst C (after steaming) as used in Example 5 is charged into a Hastelloy C reactor having an inner diameter of 17 mm$\phi$. The conversion reaction of a $C_4$ raffinate-2 is conducted using the $C_4$ raffinate-2 as used in Example 1 as a feedstock material under conditions wherein the reaction temperature is $_{600°}$ C., the amount of the $C_4$ raffinate-2 charged into the reactor is 48.8 g/hr (WHSV=16.3 hr$^{-1}$) and the pressure is 1 kg/cm$^2$·G. The reaction gas at 30 minutes after the start of the feeding of the feedstock material is analyzed. The results are shown in Table 8.

EXAMPLE 8

The conversion reaction of a $C_4$ raffinate-2 is conducted under substantially the same conditions as in Example 7, except that the feed rate of the $C_4$ raffinate-2 is 321.8 g/hr (WHSV=107 hr$^{-1}$) and the reaction pressure is 5 kg/cm$^2$·G. The results are shown in Table 8.

Table 8 shows that in the present invention, the reaction conditions can be widely varied, depending on the types of the feedstock material and catalyst employed.

EXAMPLE 9

1 g of Catalyst A (after steaming) as used in Example 2 is diluted with 0.5 g of pulverized Raschig rings (made of porcelain) and charged into a quartz glass reactor having an inner diameter of 16 mm$\phi$. The conversion reaction is conducted using a mixture of n-butane and 1-butene as a feedstock material, and the reaction gas at 30 minutes after the start of the feeding of the feedstock material is analyzed. The reaction conditions and results are shown in Table 9.

EXAMPLE 10

1.5 g of Catalyst A (after steaming) as used in Example 2 is charged into a quartz glass reactor having an inner diameter of 16 mm$\phi$. The conversion reaction is conducted using cyclopentane as a feedstock material under conditions wherein the reaction temperature is 594° C., the amount of cyclopentane charged into the reactor is 54.9 g/hr and the pressure is atmospheric pressure. The reaction gas at 30 minutes after the start of the feeding of the feedstock material is analyzed. The yields (% by weight) at 30 minutes after the start of the reaction are as follows.

Hydrogen+methane: 0.5%,
Ethylene: 12.6%,
Ethane: 0.3%,
Propylene: 20.1%,
Propane: 1.3%,
Butenes: 12.5%,
Butanes: 0.6%, $C_5$–$C_8$ PNO: 49.7%,
$C_6$–$C_8$ A: 2.1%, and
$C_9+$: 0.2%.

EXAMPLE 11

A $H^+$ form ZSM-5 zeolite extrudate (containing 40% by weight of $SiO_2$ binder, 1.6 mmφ, purchased from Nikki-Universal Co. Ltd., Japan), wherein the zeolite of the extrudate has a $SiO_2/Al_2O_3$ molar ratio of 300, is dispersed in a 1 N aqueous sodium nitrate solution (10 cc/g-zeolite) and subjected to ion exchange treatment at room temperature for 1 hour. This ion exchange treatment is repeated thrice. Subsequently, the resultant dispersion is filtered to collect the zeolite, and the collected zeolite is washed with water and dried, thereby obtaining an $Na^+$ form ZSM-5/$SiO_2$. The obtained ZSM-5/$SiO_2$ is dispersed in a 0.002 N aqueous silver nitrate solution (10 cc/g-zeolite extrudate) and subjected to ion exchange treatment at room temperature for 2 hours. Subsequently, the resultant dispersion is filtered to collect the ZSM-5/$SiO_2$, and the collected ZSM-5/$SiO_2$ is washed with water and dried, thereby obtaining Catalyst E. The Ag content and $Ag_2O/Na_2O$ molar ratio of Catalyst E are measured by fluorescent X-ray analysis. The Ag content is 0.1% by weight. The $Ag_2O/Na_2O$ molar ratio is 0.09/0.91. Catalyst E is charged into a quartz glass reactor having an inner diameter of 16 mmφ, and subjected to steaming for 5 hours under conditions wherein the temperature is 650° C., the flow rate of steam is 27.6 g/hr and the flow rate of nitrogen gas is 140 Ncc/min.

The amount of protons in Catalyst E after steaming is measured by the liquid phase ion exchange/filtrate titration method, and found to be 0.003 mmol/g. 10 g of Catalyst E after steaming is charged into a Hastelloy C reactor having an inner diameter of 17 mmφ. The conversion reaction of a $C_4$ raffinate-2 is conducted using the $C_4$ raffinate-2 as used in Example 1 as a feedstock material under conditions wherein the reaction temperature is 580° C., the amount of the $C_4$ raffinate-2 charged into the reactor is 147 g/hr (WHSV=14.7 $hr^{-1}$) and the pressure is 2 kg/cm²·G. The results are shown in Table 10.

Comparative Example 5

The $H^+$ form ZSM-5 zeolite extrudate as used in Example 11, wherein the zeolite of the extrudate has a $SiO_2/Al_2O_3$ molar ratio of 300, is subjected to steaming under substantially the same conditions as in Example 11, thereby obtaining Comparative Catalyst C'. 12 g of Comparative Catalyst C' is charged into a Hastelloy C reactor having an inner diameter of 17 mmφ. The conversion reaction of a $C_4$ raffinate-2 is conducted using the $C_4$ raffinate-2 as used in Example 1 as a feedstock material under conditions wherein the reaction temperature is 580° C., the amount of the $C_4$ raffinate-2 charged into the reactor is 127 g/hr (WHSV=10.6 $hr^{-1}$) and the pressure is 2 kg/cm²·G. The results are shown in Table 10.

Table 10 clearly shows that the amount of the coke generated during the reaction performed by the method of the present invention using Catalyst E is small, as compared to the amount of the coke generated during the reaction performed using Comparative Catalyst C', and that the change in yields of the lower olefins with the lapse of time with respect to the reaction using Catalyst E is small, as compared to that with respect to the reaction using Comparative Catalyst C'.

EXAMPLE 12

A $H^+$ form ZSM-5 zeolite extrudate (containing 30% by weight of $SiO_2$ binder, 1.6 mmφ, purchased from Nikki-Universal Co. Ltd., Japan), wherein the zeolite of the extrudate has a $SiO_2/Al_2O_3$ molar ratio of 300, is dispersed in a in aqueous sodium nitrate solution (10 cc/g-zeolite) and subjected to ion-exchange treatment at room temperature for 1 hour. This ion-exchange treatment is repeated twice. Subsequently, the resultant dispersion is filtered to collect the zeolite, and the collected zeolite is washed with water and dried, thereby obtaining an $Na^+$ form ZSM-5/$SiO_2$. The obtained ZSM-5/$SiO_2$ is dispersed in a 0.001 N aqueous silver nitrate solution (10 cc/g-zeolite extrudate) and subjected to ion exchange treatment at room temperature for 2 hours. Subsequently, the resultant dispersion is filtered to collect the ZSM-5/$SiO_2$, and the collected ZSM-5/$SiO_2$ is washed with water and dried, thereby obtaining Catalyst F. The Ag content and $Ag_2O/Na_2O$ molar ratio of Catalyst F are measured by fluorescent X-ray analysis. The Ag content is 0.06% by weight. The $Ag_2O/Na_2O$ molar ratio is 0.05/0.95. Catalyst F is charged into a quartz glass reactor having an inner diameter of 16 mmφ, and subjected to steaming for 5 hours under conditions wherein the temperature is 650° C., the flow rate of steam is 27.6 g/hr and the flow rate of nitrogen gas is 140 Ncc/min.

The amount of protons in Catalyst F after steaming is measured by the liquid phase ion exchange/filtrate titration method, and found to be 0.003 mmol/g. 30 g of Catalyst F after steaming is charged into a Hastelloy C reactor having an inner diameter of 27 mmφ. The reaction is conducted, using the $C_4$ raffinate-2 as used in Example 1 as a feedstock material, for 24 hours under conditions wherein the reaction temperature is 580° C., the amount of the $C_4$ raffinate-2 charged is 240 g/hr (WHSV=8 $hr^{-1}$) and the reaction pressure is 2 kg/cm²·G. After completion of the reaction, the catalyst regeneration operation is conducted under the following conditions:

Temperature: from 500 to 550° C.,
Pressure: 5 kg/cm²·G,
Flow rate of nitrogen gas+air: 1077 Nl/hr,
Oxygen concentration: 0.8 to 1.2% by volume,
Flow rate of steam (added for accelerating the regeneration deactivation of the catalyst): 26 g/hr, and
Time for regeneration: 20 hours.

The cycle including the above-mentioned reaction step (for 24 hours) and regeneration step (for 20 hours) is repeated 18 times. During the reaction step, the reaction gas is analyzed every 4 hours. The average value of the yields in the 24-hour reaction steps according to the number of cycles are shown in Table 11. Table 11 clearly shows that the yields of lower olefins are extremely stable, even if the reaction/regeneration cycle is repeatedly performed.

EXAMPLE 13

The conversion reaction of a $C_4$-raffinate-2 is conducted under substantially the same conditions as in Example 8.

The resultant reaction product is cooled to 10° C. at the outlet of the reactor by means of a heat exchanger, and introduced into a flash drum for gas-liquid separation, thereby separating a liquid from a gas. The separated liquid is charged into a distillation column and subjected to distillation, thereby separating a $C_5$–$C_6$ fraction. The separated $C_5$–$C_6$ fraction is recycled to the reactor. After the conditions for the catalytic conversion reaction are stabilized, the amount of the $C_4$ raffinate-2 charged into the reactor and the amount of the $C_5$–$C_6$ fraction recycled to the reactor are 260.3 g/hr and 61.5 g/hr, respectively. The yields (% by weight) based on the amount of the $C_4$ raffinate-2 are as follows.

Hydrogen+methane: 1.4%,
Ethylene: 7.2%,
Ethane: 0.9%,
Propylene: 26.4%,
Propane: 2.5%,
Butenes: 28.6%,
Butanes: 21.8%,
$C_5$–$C_8$ PNO: 5.0%,
$C_6$–$C_8$ A: 4.7%, and
$C_9$+: 1.5%.

Comparison of the above-mentioned results with the results in Example 8 clearly shows that the yields of the lower olefins are improved by performing the recycling of the $C_5$–$C_6$ fraction.

EXAMPLE 14

The catalytic conversion reaction of a $C_4$ raffinate-2 is conducted under substantially the same conditions as in Example 2, except that the reaction temperature is 600° C. and the WHSV is 30 hr$^{-1}$. The resultant reaction product discharged from the outlet of the reactor is charged into a separation tower. The Components having a boiling point lower than propane are separated and removed, and the remaining fraction having a high boiling point is subjected to steam cracking. That is, the above-mentioned fraction having a high boiling point is mixed with steam (weight ratio of steam to hydrocarbon (steam/hydrocarbon)=0.35), and the resultant mixture is preheated to 600° C., charged into a thermal cracking coil and subjected to steam cracking under conditions wherein the residence time in the coil is 0.6 second and the cracking temperature (the temperature at the outlet of the coil) is 796° C. The yields in the total process are shown in Table 12.

Comparative Example 6

A $C_4$ raffinate-2 is subjected to steam cracking by the following procedure. A $C_4$ raffinate-2 is mixed with steam (weight ratio of steam to hydrocarbon (steam/hydrocarbon) =0.35), and the resultant mixture is preheated to 600° C., charged into a thermal cracking coil and subjected to steam cracking under conditions wherein the residence time in the coil is 0.6 second and the cracking temperature (the temperature at the outlet of the coil) is 802° C. The results are shown in Table 12.

Table 12 clearly shows that the yields of propylene and ethylene are extremely increased by combining the catalytic conversion and the thermal cracking.

EXAMPLE 15

A Na$^+$ form ZSM-5 zeolite having a $SiO_2/Al_2O_3$ molar ratio of 3,000 is dispersed in a 0.05 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120° C. for 5 hours, followed by calcination in air at 550° C., thereby obtaining Catalyst G. The Ag content and $Ag_2O/Na_2O$ molar ratio of Catalyst G are measured by fluorescent X-ray analysis. The Ag content is 0.1% by weight. The $Ag_2O/Na_2O$ molar ratio is 0.83/0.17. 4 g of Catalyst G is charged into a quartz glass reactor having an inner diameter of 16 mm$\phi$, and steamed for 5 hours under conditions wherein the temperature is 650° C., the flow rate of steam is 27.6 g/hr and the flow rate of nitrogen gas is 140 Ncc/min. The amount of protons in Catalyst G after steaming, which is measured by the liquid phase ion exchange/filtrate titration method, is 0.002 mmol/g. 2.5 g of Catalyst G after steaming is charged into a quartz glass reactor having an inner diameter of 16 mm$\phi$. The conversion reaction of a $C_4$ raffinate-2 is conducted under substantially the same conditions as in Example 1, except that the reaction time is 24 hours. The results are shown in Table 13.

Comparative Example 7

A Na$^+$ form ZSM-5 zeolite having a $SiO_2/Al_2O_3$ molar ratio of 5,500 is dispersed in a 0.05 N aqueous silver nitrate solution (10 cc/g-zeolite) and subjected to ion exchange treatment at room temperature for 2 hours. Subsequently, the resultant dispersion is filtered to collect the zeolite, and the collected zeolite is washed with water and dried at 120 C. for 5 hours, followed by calcination in air at 550° C., thereby obtaining Comparative Catalyst D'. The Ag content and $Ag_2O/Na_2O$ molar ratio of Comparative Catalyst D' are measured by fluorescent X-ray analysis. The Ag content is 0.05% by weight. The $Ag_2O/Na_2O$ molar ratio is 0.77/0.23. 4 g of Comparative Catalyst D' is charged into a quartz glass reactor having an inner diameter of 16 mm$\phi$, and steamed for 5 hours under conditions wherein the temperature is 650° C., the flow rate of steam is 27.6 g/hr and the flow rate of nitrogen gas is 140 Ncc/min. The amount of protons in Comparative Catalyst D' after steaming, which is measured by the liquid phase ion exchange/filtrate titration method, is 0.002 mmol/g. 2.5 g of Comparative Catalyst D' after steaming is charged into a quartz glass reactor having an inner diameter of 16 mm$\phi$. The conversion reaction of a $C_4$ raffinate-2 is conducted under substantially the same conditions as in Example 15. The results are shown in Table 13.

EXAMPLE 16

1.0g of catalyst A (after steaming) as used in Example 2 is diluted with 0.5 g of pulverized Raschig rings (made of porcelain) and charged into a quartz glass reactor having an inner diameter of 16 mm$\phi$.

The conversion reaction is conducted using a $C_5$ raffinate (obtained from a thermal cracking product of naphtha) as a feedstock material under conditions wherein the amount of the $C_5$ raffinate charged into the reactor is 46.7 g/hr, the reaction temperature is 600° C. and the pressure is atmospheric pressure. The composition (% by weight) of the $C_5$ raffinate is as follows.

Butenes: 0.4,
Butadiene: 0.2,
Isopentane: 29.3,
n-pentane: 47.5,
Pentenes: 22.3,
Cyclopentane: 0.1,
Cyclopentadiene: 0.2

The reaction gas at 30 minutes after the start of the feeding of the feedstock material is analyzed. The yields at 30 minutes after the start of the feeding of the feedstock material are as follows.

Hydrogen+methane: 1.4,
Ethylene: 7.1,
Ethane: 1.6,
Propylene: 12.7
Propane: 0.8,
Butenes: 6.9,
Butanes: 0.2,
Pentene: 3.4,
Pentane: 62.4,
$C_6$–$C_8$ PNO: 1.2,
$C_6$–$C_8$ A: 2.2%, and
$C_9$+0.1.

Further, the (ethylene+propylene)/(hydrogen+methane) molar ratio is 4.1.

Comparative Example 8

1 g of Catalyst A (after steaming) as used in Example 2 is diluted with 0.5 g of pulverized Raschig rings (made of porcelain) and charged into a quartz glass reactor having an inner diameter of 16 mmφ. The conversion reaction is conducted using a mixture of n-butane and 1-butene (1-butene content: 15.0% by weight) as a feedstock material, and the reaction gas at 30 minutes after the start of the feeding of the feedstock material is analyzed. The reaction conditions and results are shown in Table 14.

TABLE 1

(The composition of $C_4$ raffinate-2 (% by wt.))

| Component | Concentration (% by wt.) |
|---|---|
| Acetylene | 0.1 |
| Propylene | 0.3 |
| Propane | 0.2 |
| Butadiene | 1.1 |
| Butenes | 77.1 |
| Butanes | 19.7 |
| Pentenes | 0.3 |
| Pentanes | 0.9 |
| Octenes | 0.3 |
| Total | 100 |

TABLE 2

(Example 1)

| Catalyst | Catalyst A | | | |
|---|---|---|---|---|
| Reaction conditions | $C_4$ raffinate-2 (600° C., WHSV = 41.7 hr$^{-1}$) | | | |
| Time on streams (hr) | 0.5 | 10 | 25 | 48 |
| Yield (% by wt.) | | | | |
| Hydrogen + methane | 1.1 | 0.9 | 0.6 | 0.5 |
| Ethylene | 10.6 | 8.7 | 7.0 | 4.5 |
| Ethane | 0.5 | 0.5 | 0.2 | 0.2 |
| Propylene | 30.0 | 29.0 | 27.3 | 21.5 |
| Propane | 1.7 | 1.3 | 1.0 | 0.5 |
| Butenes | 20.8 | 24.3 | 28.5 | 37.9 |
| Butanes | 21.4 | 21.6 | 21.8 | 21.5 |
| $C_5$–$C_8$ PNO* | 9.2 | 10.0 | 10.7 | 11.6 |
| $C_6$–$C_8$ A** | 4.4 | 3.5 | 2.7 | 1.7 |
| $C_9$ + hydrocarbons | 0.3 | 0.2 | 0.2 | 0.1 |
| Ethylene + propylene | 40.6 | 37.7 | 34.3 | 26.0 |
| (Ethylene + propylene)/ (hydrogen + methane) molar ratio | 8.6 | 10.1 | 13.8 | 14.5 |

*$C_5$–$C_8$ non-aromatic hydrocarbons.
**$C_6$–$C_8$ aromatic hydrocarbons.

TABLE 3

(Comparative Example 1)

| Catalyst | H$^+$ZSM-5 | | | |
|---|---|---|---|---|
| Reaction conditions | $C_4$ raffinate-2 (600° C., WHSV = 41.7 hr$^{-1}$) | | | |
| Time on streams (hr) | 0.5 | 10 | 20.5 | 24 |
| Yield (% by wt.) | | | | |
| Hydrogen + methane | 0.8 | 0.7 | 0.3 | 0.3 |
| Ethylene | 8.7 | 6.7 | 3.1 | 2.1 |
| Ethane | 0.3 | 0.3 | 0.1 | 0.1 |
| Propylene | 28.4 | 26.5 | 18.3 | 14.7 |
| Propane | 1.5 | 1.3 | 0.7 | 0.6 |
| Butenes | 26.3 | 29.0 | 43.3 | 49.5 |
| Butanes | 21.2 | 22.0 | 21.7 | 21.5 |
| $C_5$–$C_8$ PNO* | 8.7 | 10.5 | 11.0 | 10.1 |
| $C_6$–$C_8$ A** | 3.9 | 2.9 | 1.4 | 1.0 |
| $C_9$ + hydrocarbons | 0.2 | 0.1 | 0.1 | 0.1 |
| Ethylene + propylene | 37.1 | 33.2 | 21.4 | 16.8 |
| (Ethylene + propylene)/ (hydrogen + methane) molar ratio | 11.4 | 12.2 | 15.9 | 15.8 |

*$C_5$–$C_8$ non-aromatic hydrocarbons.
**$C_6$–$C_8$ aromatic hydrocarbons.

TABLE 4

(Example 2)

| Catalyst | Steamed Catalyst A | | | |
|---|---|---|---|---|
| Reaction conditions | $C_4$ raffinate-2 (600° C., WHSV = 37.5 hr$^{-1}$) | | | |
| Time on streams (hr) | 0.5 | 10 | 25 | 48 |
| Yield (% by wt.) | | | | |
| Hydrogen + methane | 1.0 | 0.8 | 0.7 | 0.6 |
| Ethylene | 11.6 | 10.2 | 9.2 | 7.9 |
| Ethane | 0.4 | 0.4 | 0.4 | 0.4 |
| Propylene | 29.9 | 29.8 | 29.4 | 27.5 |
| Propane | 1.8 | 1.4 | 1.1 | 0.8 |
| Butenes | 19.3 | 21.9 | 24.1 | 27.8 |
| Butanes | 21.8 | 21.8 | 21.8 | 21.4 |
| $C_5$–$C_8$ PNO* | 8.8 | 9.6 | 10.0 | 11.0 |
| $C_6$–$C_8$ A** | 5.1 | 3.9 | 3.1 | 2.5 |
| $C_9$ + hydrocarbons | 0.3 | 0.2 | 0.2 | 0.1 |
| Ethylene + propylene | 41.5 | 40.0 | 38.6 | 35.4 |

TABLE 4-continued (Example 2)

| | | | | |
|---|---|---|---|---|
| (Ethylene + propylene)/(hydrogen + methane) molar ratio | 8.8 | 11.9 | 14.3 | 15.3 |

*$C_5$–$C_8$ non-aromatic hydrocarbons.
**$C_6$–$C_8$ aromatic hydrocarbons.

TABLE 5

(Example 3)

| Catalyst | Steamed Catalyst B | | | |
|---|---|---|---|---|
| Reaction conditions | $C_4$ raffinate-2 (600° C., WHSV = 37.5 hr$^{-1}$) | | | |
| Time on streams (hr) | 0.5 | 10 | 20 | 24 |
| Yield (% by wt.) | | | | |
| Hydrogen + methane | 0.7 | 0.6 | 0.5 | 0.5 |
| Ethylene | 11.4 | 7.7 | 6.6 | 5.6 |
| Ethane | 0.4 | 0.3 | 0.2 | 0.2 |
| Propylene | 31.0 | 28.2 | 26.7 | 24.7 |
| Propane | 1.9 | 0.9 | 0.7 | 0.6 |
| Butenes | 19.7 | 27.7 | 30.8 | 34.1 |
| Butanes | 20.0 | 19.8 | 19.6 | 19.4 |
| $C_5$–$C_8$ PNO* | 9.4 | 11.4 | 12.0 | 12.4 |
| $C_6$–$C_8$ A** | 5.2 | 3.2 | 2.7 | 2.4 |
| $C_9$ + hydrocarbons | 0.3 | 0.2 | 0.2 | 0.1 |
| Ethylene + propylene | 42.4 | 35.9 | 33.3 | 30.3 |
| (Ethylene + propylene)/(hydrogen + ethylene) molar ratio | 12.4 | 12.6 | 14.7 | 15.2 |

*$C_5$–$C_8$ non-aromatic hydrocarbons.
**$C_6$–$C_8$ aromatic hydrocarbons.

TABLE 6

(Comparative Example 3)

| Catalyst | Steamed Comparative Catalyst A' | | | |
|---|---|---|---|---|
| Reaction conditions | $C_4$ raffinate-2 (600° C., WHSV = 41.7 hr$^{-1}$) | | | |
| Time on streams (hr) | 0.5 | 10 | 20 | 24 |
| Yield (% by wt.) | | | | |
| Hydrogen + methane | 0.9 | 0.5 | 0.4 | 0.2 |
| Ethylene | 12.7 | 5.5 | 1.5 | 0.5 |
| Ethane | 0.6 | 0.2 | 0.1 | 0.0 |
| Propylene | 28.9 | 24.5 | 11.5 | 6.5 |
| Propane | 2.6 | 0.8 | 0.3 | 0.2 |

TABLE 6-continued (Comparative Example 3)

| | | | | |
|---|---|---|---|---|
| Butenes | 17.3 | 31.7 | 53.3 | 63.2 |
| Butanes | 22.6 | 22.8 | 22.4 | 22.3 |
| $C_5$–$C_8$ PNO* | 8.4 | 11.8 | 9.7 | 6.6 |
| $C_6$–$C_8$ A** | 5.6 | 2.0 | 0.7 | 0.4 |
| $C_9$ + hydrocarbons | 0.4 | 0.2 | 0.1 | 0.1 |
| Ethylene + propylene | 41.6 | 30.0 | 13.0 | 7.0 |
| (Ethylene + propylene)/(hydrogen + methane) molar ratio | 9.3 | 14.9 | 10.1 | 9.1 |

*$C_5$–$C_8$ non-aromatic hydrocarbons.
**$C_6$–$C_8$ aromatic hydrocarbons.

TABLE 7

(Comparative Example 4)

| Catalyst | Steamed Comparative Catalyst B' | | | |
|---|---|---|---|---|
| Reaction conditions | $C_4$ raffinate-2 (600° C., WHSV = 17.7 hr$^{-1}$) | | | |
| Time on streams (hr) | 0.5 | 10 | 20 | 24 |
| Yield (% by wt.) | | | | |
| Hydrogen + methane | 0.8 | 0.7 | 0.5 | 0.5 |
| Ethylene | 11.4 | 5.2 | 1.7 | 1.1 |
| Ethane | 0.4 | 0.2 | 0.1 | 0.1 |
| Propylene | 29.4 | 25.0 | 14.1 | 9.3 |
| Propane | 3.0 | 0.8 | 0.4 | 0.3 |
| Butenes | 18.6 | 31.8 | 49.7 | 57.8 |
| Butanes | 21.9 | 21.7 | 21.1 | 21.4 |
| $C_5$–$C_8$ PNO* | 8.8 | 11.9 | 11.3 | 8.8 |
| $C_6$–$C_8$ A** | 5.5 | 2.5 | 1.0 | 0.6 |
| $C_9$ + hydrocarbons | 0.2 | 0.2 | 0.1 | 0.1 |
| Ethylene + propylene | 40.8 | 30.2 | 15.8 | 10.4 |
| (Ethylene + propylene)/(hydrogen + methane) molar ratio | 9.2 | 10.2 | 9.1 | 6.8 |

*$C_5$–$C_8$ non-aromatic hydrocarbons.
**$C_6$–$C_8$ aromatic hydrocarbons.

TABLE 8

| Example | 4 | 5 | 6 | 7 | 8 |
|---|---|---|---|---|---|
| Feedstock | 1-Hexene | 1-Butene | 1-Butene | $C_4$ Raffinate | $C_4$ Raffinate |
| Reaction temp. (° C.) | 550 | 600 | 600 | 600 | 600 |
| Pressure (K/G) | 0 | 0 | 0 | 1 | 5 |
| WHSV (hr$^{-1}$) | 93 | 9.5 | 10.2 | 16.3 | 107 |
| Yield (% by wt.) | | | | | |
| Hydrogen + methane | 1.1 | 1.5 | 1.4 | 1.7 | 0.8 |
| Ethylene | 8.8 | 11.9 | 10.2 | 9.7 | 5.8 |
| Ethane | 1.1 | 0.3 | 0.3 | 0.8 | 0.5 |
| Propylene | 45.0 | 36.4 | 34.9 | 26.2 | 21.2 |
| Propane | 0.0 | 1.6 | 1.1 | 1.7 | 1.9 |
| Butenes | 20.6 | 25.4 | 30.4 | 19.7 | 22.4 |
| Butanes | 0.4 | 3.7 | 3.3 | 20.4 | 21.5 |
| $C_5$–$C_8$ PNO* | 20.1 | 11.9 | 13.3 | 12.6 | 20.8 |
| $C_6$–$C_8$ A** | 2.5 | 6.6 | 4.6 | 6.3 | 3.9 |
| $C_9$+ hydrocarbons | 0.4 | 0.7 | 0.5 | 0.9 | 1.2 |

TABLE 8-continued

| Example | 4 | 5 | 6 | 7 | 8 |
|---|---|---|---|---|---|
| Ethylene + propylene | 53.8 | 48.3 | 45.1 | 35.9 | 27.0 |
| (Ethylene + propylene) /(hydrogen + methane) molar ratio | 15.7 | 8.0 | 8.4 | 5.3 | 9.5 |

*$C_5$–$C_8$ non-aromatic hydrocarbons.
**$C_6$–$C_8$ aromatic hydrocarbons.

TABLE 9

(Example 9)

| Feedstock | Butane/Butene | Butane/Butene | Butane/Butene |
|---|---|---|---|
| Olefin content of the feedstock (% by wt.) | 33.4 | 55.0 | 91.1 |
| Reaction temp. (° C.) | 601 | 599 | 600 |
| Pressure (K/G) | 0 | 0 | 0 |
| WHSV ($hr^{-1}$) | 34.2 | 36.1 | 37.2 |
| Yield (% by wt.) | | | |
| Hydrogen + methane | 1.2 | 1.3 | 1.3 |
| Ethylene | 4.4 | 7.9 | 12.9 |
| Ethane | 1.1 | 0.8 | 0.4 |
| Propylene | 11.0 | 20.9 | 35.9 |
| Propane | 0.6 | 1.0 | 1.6 |
| Butenes | 10.5 | 16.3 | 25.1 |
| Butanes | 67.5 | 43.3 | 3.9 |
| $C_5$–$C_8$ PNO* | 2.3 | 5.6 | 12.6 |
| $C_6$–$C_8$ A** | 1.4 | 2.8 | 5.9 |
| $C_9$ + hydrocarbons | 0.0 | 0.1 | 0.4 |
| Ethylene + propylene | 15.4 | 28.8 | 48.8 |
| (Ethylene + propylene)/(hydrogen + methane) molar ratio | 3.9 | 5.8 | 8.4 |

*$C_5$–$C_8$ non-aromatic hydrocarbons.
**$C_6$–$C_8$ aromatic hydrocarbons.

TABLE 10

| | Example 11 | | | Comparative Example 5 | | |
|---|---|---|---|---|---|---|
| Catalyst | Catalyst E (steamed) | | | Comparative catalyst C' (steamed) | | |
| Reaction conditions | 580° C., 2 K/G, WHSV = 14.7 ($hr^{-1}$) | | | 580° C., 2 K/G, WHSV = 10.6 ($hr^{-1}$) | | |
| Time on streams (hr) | 5 | 15 | 24 | 4 | 14 | 23 |
| Yield (% by wt.) | | | | | | |
| Hydrogen + methane | 0.8 | 0.6 | 0.6 | 1.4 | 0.8 | 0.5 |
| Ethylene | 7.5 | 6.3 | 5.1 | 7.0 | 5.0 | 2.4 |
| Ethane | 0.6 | 0.5 | 0.4 | 0.7 | 0.4 | 0.3 |
| Propylene | 21.8 | 22.3 | 22.2 | 21.6 | 22.4 | 17.7 |
| Propane | 3.2 | 2.3 | 1.5 | 2.2 | 1.3 | 0.7 |
| Butenes | 18.3 | 21.6 | 24.8 | 19.6 | 25.0 | 36.5 |
| Butanes | 22.3 | 21.8 | 21.5 | 21.4 | 21.1 | 20.5 |
| $C_5$–$C_8$ PNO* | 17.5 | 18.7 | 19.2 | 17.9 | 19.2 | 18.6 |
| $C_6$–$C_8$ A** | 7.1 | 5.1 | 4.0 | 7.0 | 4.1 | 2.3 |
| $C_9^+$ hydrocarbons | 0.9 | 0.8 | 0.7 | 1.2 | 0.7 | 0.6 |
| Ethylene + propylene | 29.3 | 28.6 | 27.3 | 28.6 | 27.4 | 20.1 |
| Yield of coke (ppm) | | 470 | | | 800 | |
| (Ethylene + propylene)/(hydrogen + methane) molar ratio | 8.1 | 10.9 | 12.1 | 5.1 | 8.6 | 10.0 |

*$C_5$–$C_8$ non-aromatic hydrocarbons.
**$C_6$–$C_8$ aromatic hydrocarbons.

TABLE 11

(Example 12)

| Number of reaction cycles | Conversion of butenes (wt. %) (average conversion for 24-hour reaction) | Average yield for 24-hour reaction (wt %) | |
|---|---|---|---|
| | | Ethylene | Propylene |
| 1 | 73 | 6.5 | 22.7 |
| 4 | 73 | 6.3 | 22.1 |
| 7 | 72 | 6.0 | 22.5 |
| 10 | 72 | 6.4 | 22.4 |
| 13 | 72 | 6.1 | 22.2 |
| 16 | 72 | 6.1 | 22.4 |
| 18 | 72 | 6.2 | 22.3 |

TABLE 12

| | Example 14 | Comp. Ex. 6 |
|---|---|---|
| Yield (% by wt.) | | |
| Hydrogen + methane | 9.9 | 17.6 |
| Ethylene | 22.5 | 17.6 |
| Ethane | 2.0 | 2.3 |
| Propylene | 38.8 | 16.6 |
| Propane | 2.1 | 0.3 |
| Butadiene | 1.9 | 7.2 |
| Butanes + butenes | 6.8 | 9.7 |
| $C_5$–$C_8$ PNO* | 2.0 | 4.5 |
| $C_6$–$C_8$ A** | 10.1 | 17.9 |
| $C_9$ + hydrocarbons | 3.9 | 6.3 |
| Ethylene + propylene | 61.3 | 34.2 |

*$C_5$–$C_8$ non-aromatic hydrocarbons.
**$C_6$–$C_8$ aromatic hydrocarbons.

TABLE 13

| | Example 15 | | Comp. Ex. 7 | |
|---|---|---|---|---|
| Catalyst | Catalyst G (steamed) | | Comparative Catalyst D' (steamed) | |
| Reaction conditions | 600° C., WHSV = 6 $hr^{-1}$ | | 600° C., WHSV = 6 $hr^{-1}$ | |
| Time on streams (hr) | 0.5 | 24 | 0.5 | 24 |
| Yield (% by wt.) | | | | |
| Hydrogen + methane | 1.0 | 0.8 | 0.3 | 0.3 |
| Ethylene | 9.0 | 7.3 | 3.4 | 2.6 |
| Ethane | 0.4 | 0.3 | 0.1 | 0.1 |
| Propylene | 28.5 | 26.6 | 16.9 | 13.8 |
| Propane | 1.2 | 0.8 | 0.3 | 0.3 |
| Butenes | 23.9 | 28.7 | 46.2 | 51.7 |
| Butanes | 20.0 | 19.9 | 19.7 | 19.5 |
| $C_5$–$C_8$ PNO* | 11.0 | 12.0 | 11.6 | 10.5 |
| $C_6$–$C_8$ A** | 4.6 | 3.3 | 1.3 | 1.0 |

TABLE 13-continued

|  | Example 15 |  | Comp. Ex. 7 |  |
|---|---|---|---|---|
| $C_9$ + hydrocarbons | 0.4 | 0.3 | 0.2 | 0.2 |
| Ethylene + propylene | 37.5 | 33.9 | 20.3 | 16.4 |

*$C_5$–$C_8$ non-aromatic hydrocarbons.
**$C_6$–$C_8$ aromatic hydrocarbons.

TABLE 14

(Comparative Example 8)

| Feedstock | Butane/Butene |
|---|---|
| Olefin content of the feedstock (% by wt.) | 15.0 |
| Reaction temp. (° C.) | 601 |
| Pressure (K/G) | 0 |
| WHSV (hr$^{-1}$) | 34.2 |
| Yield (% by wt.) | |
| Hydrogen + methane | 1.1 |
| Ethylene | 2.0 |
| Ethane | 1.0 |
| Propylene | 4.9 |
| Propane | 0.3 |
| Butenes | 4.7 |
| Butanes | 84.4 |
| $C_5$–$C_8$ PNO* | 1.0 |
| $C_6$–$C_8$ A** | 0.6 |
| $C_9$ + hydrocarbons | 0.0 |
| Ethylene + propylene | 3.6 |
| (Ethylene + propylene)/(hydrogen + methane) molar ratio | 1.8 |

*$C_5$–$C_8$ non-aromatic hydrocarbons.
**$C_6$–$C_8$ aromatic hydrocarbons.

TABLE 15

(Comparison of the change in the activity of the catalyst caused by steaming)

|  | Activity* prior to steaming | Activity* after steaming | Ratio of the change in the activity of the catalyst |
|---|---|---|---|
| Examples 1 and 2 | 54.6 | 51.9 | 0.95 |
| Comparative Examples 1 and 2 | 44.9 | 21.1 | 0.47 |

*activity = reaction rate constant (hr$^{-1}$)

Industrial Applicability

In the method of the present invention, not only can ethylene and propylene be produced in high yield, but also the resistance of the zeolite-containing catalyst to deactivation is high, so that the production of ethylene and propylene can be stably conducted for a prolonged period of time. In addition, by the method of the present invention, in the catalytic conversion of a hydrocarbon feedstock, it becomes possible to suppress the by-production of hydrogen, methane, ethane and aromatic hydrocarbons, and improve the selectivity for ethylene and propylene.

Further, the method of the present invention is advantageous in that there is no need to use a reactor system having a complicated system adapted for frequently regenerating the catalyst, and the desired ethylene and propylene can be produced using a simple reactor system, such as a fixed-bed, adiabatic reactor.

What is claimed is:

1. A method for producing ethylene and propylene from a hydrocarbon feedstock by catalytic conversion, which comprises:
   contacting, in a reactor, a hydrocarbon feedstock comprising 20% by weight or more, based on the weight of said hydrocarbon feedstock, of at least one $C_4$–$C_{12}$ olefin with a zeolite-containing catalyst to thereby effect a catalytic conversion reaction of said at least one $C_4$–$C_{12}$ olefin, thereby obtaining a reaction mixture containing ethylene and propylene,
   wherein the zeolite in said zeolite-containing catalyst satisfies the following requirements (1), (2), (3) and (4):
   (1) said zeolite is an intermediate pore size zeolite having a pore size of from 5 to 6.5 Å,
   (2) said zeolite contains substantially no proton,
   (3) said zeolite contains at least one metal selected from the group consisting of metals belonging to Group IB of the Periodic Table, and
   (4) said zeolite has an $SiO_2/Al_2O_3$ molar ratio of from 200 to 5,000; and
   separating the ethylene and propylene from said reaction mixture.

2. The method according to claim 1, wherein the separation of the ethylene and propylene from said reaction mixture is conducted by separating said reaction mixture into fraction A comprised mainly of hydrogen and hydrocarbons having 1 to 3 carbon atoms and fraction B comprised mainly of at least one hydrocarbon having 4 or more carbon atoms, followed by separation of the ethylene and propylene from said fraction A.

3. The method according to claim 2, which further comprises separating said fraction B into fraction $B_1$ comprised mainly of at least one hydrocarbon having 4 to 8 carbon atoms and fraction $B_2$ comprised mainly of at least one hydrocarbon having 9 or more carbon atoms, and recycling at least a part of said fraction $B_1$ to said reactor so as to use said at least a part of said fraction $B_1$ as a part of said hydrocarbon feedstock.

4. The method according to claim 2, wherein said fraction B is subjected to steam cracking to thereby obtain a steam cracking product containing ethylene and propylene, followed by separation of the ethylene and propylene from said steam cracking product.

5. The method according to any one of claims 1 to 4, wherein said hydrocarbon feedstock comprises 50% by weight or more, based on the weight of said hydrocarbon feedstock, of at least one $C_4$–$C_{12}$ olefin.

6. The method according to any one of claims 1 to 4, wherein said zeolite further contains at least one metal selected from the group consisting of alkali metals and alkaline earth metals.

7. The method according to any one of claims 1 to 4, wherein, prior to the contacting with said hydrocarbon feedstock, said zeolite-containing catalyst is heated in the presence of steam at a temperature of 500° C. or more.

8. The method according to any one of claims 1 to 4, wherein said at least one metal selected from the group consisting of metals belonging to Group IB of the Periodic Table is silver.

9. The method according to any one of claims 1 to 4, wherein said zeolite is selected from the group consisting of zeolites belonging to the ZSM-5 zeolite family.

10. The method according to any one of claims 1 to 4, wherein said catalytic conversion reaction of said at least one $C_4$–$C_{12}$ olefin is effected at a temperature of from 400 to 700° C. under a pressure of from 0.1 to 10 atm. and at a weight hourly space velocity of from 1 to 1000 hr$^{-1}$.

11. The method according to any one of claims 1 to 4, wherein said catalytic conversion reaction of said at least one $C_4$–$C_{12}$ olefin is effected at a temperature of from 400 to 700° C. and at a weight hourly space velocity of from 1 to 1000 $hr^{-1}$, and wherein said hydrocarbon feedstock is a mixture thereof with a diluent gas, and the partial pressure of said hydrocarbon feedstock in said mixture is from 0.1 to 10 atm.

* * * * *